United States Patent [19]

Briggs et al.

[11] Patent Number: 5,449,653
[45] Date of Patent: * Sep. 12, 1995

[54] CATALYSTS AND PROCESSES USEFUL IN PRODUCING 1,3-DIOLS AND/OR 3-HYDROXYALDEHYDES

[75] Inventors: John R. Briggs; John M. Maher, both of Charleston; Arnold M. Harrison, South Charleston, all of W. Va.

[73] Assignee: Union Carbide Chemicals & Plastics Technology Corporation, Danbury, Conn.

[*] Notice: The portion of the term of this patent subsequent to Jul. 6, 2010 has been disclaimed.

[21] Appl. No.: 14,389

[22] Filed: Feb. 5, 1993

Related U.S. Application Data

[60] Division of Ser. No. 670,876, Mar. 18, 1991, Pat. No. 5,210,318, which is a continuation-in-part of Ser. No. 519,273, May 4, 1990, abandoned.

[51] Int. Cl.$^6$ .............................................. B01J 31/00
[52] U.S. Cl. .................................. 502/166; 502/161; 502/162; 502/164; 502/167
[58] Field of Search ...................... 502/161, 164, 166

[56] References Cited

U.S. PATENT DOCUMENTS

| | | | |
|---|---|---|---|
| 3,456,017 | 7/1969 | Smith | 260/602 |
| 3,463,819 | 8/1969 | Smith | 260/602 |
| 3,687,981 | 8/1972 | Lawrence et al. | 260/635 |
| 4,101,564 | 7/1978 | Poist | 260/429.7 |
| 4,302,401 | 11/1981 | Oswald | 568/454 |
| 4,322,355 | 3/1982 | Horvitz et al. | 260/340 |
| 4,599,206 | 7/1986 | Billig et al. | 558/85 |
| 4,668,651 | 5/1987 | Billig et al. | 502/158 |
| 4,717,775 | 1/1988 | Billig et al. | 568/454 |
| 4,769,498 | 9/1988 | Billig et al. | 568/454 |
| 4,774,361 | 9/1988 | Maher et al. | 568/454 |
| 4,873,378 | 10/1989 | Murphy et al. | 568/867 |
| 4,873,379 | 10/1989 | Murphy | 568/867 |
| 4,885,401 | 12/1989 | Billig et al. | 260/448 C |
| 4,935,554 | 6/1990 | Murphy et al. | 568/867 |
| 5,030,766 | 7/1991 | Briggs et al. | 568/496 |
| 5,225,387 | 7/1993 | Briggs et al. | 502/162 X |

FOREIGN PATENT DOCUMENTS

| | | |
|---|---|---|
| 0257967 | 3/1988 | European Pat. Off. . |
| 0306094 | 3/1989 | European Pat. Off. . |
| 0343944 | 11/1989 | European Pat. Off. . |

OTHER PUBLICATIONS

Chan et al., Aspects of Anionic Rhodium Complexes, Ligand Effects, Journal of Organometallic Chemistry, 279 (1985) 171–179 (No month available).

*Primary Examiner*—Asok Pal
*Attorney, Agent, or Firm*—R. J. Finnegan

[57] ABSTRACT

A process for producing a 1,3-diol, e.g., 1,3-propanediol, and/or a 3-hydroxyaldehyde, e.g., 3-hydroxypropionaldehyde, is disclosed which comprises contacting a combination of an epoxide, carbon monoxide and hydrogen in the presence of a rhodium-containing catalyst composition effective to promote the hydroformylation of the epoxide at conditions effective to form at least one of a 1,3-diol and a 3-hydroxyaldehyde. The rhodium-containing catalyst composition comprises an anionic rhodium-containing complex. A promoter component is preferably provided to enhance at least one of the rate and selectivity of the epoxide hydroformylation reaction. Rhodium-containing compositions and a processes for producing rhodium-containing compositions are also disclosed.

14 Claims, No Drawings

CATALYSTS AND PROCESSES USEFUL IN PRODUCING 1,3-DIOLS AND/OR 3-HYDROXYALDEHYDES

REALTED APPLICATION

This application is a Division of U.S. application Ser. No. 670,876 filed Mar. 18, 1991, now U.S. Pat. No. 5,210,318, which is a Continuation-in-Part of U.S. application Ser. No. 519,273 filed May 4, 1990, now abandoned.

BACKGROUND OF THE INVENTOIN

The present invention relates to the production of 1,3-diols and/or 3-hydroxyaldehydes from epoxides. More particularly, the invention relates to hydroformylation catalysts, processes for making hydroformylation catalysts and processes using hydroformylation catalysts for producing such 1-3 diols and/or 3-hydroxyaldehydes from epoxides.

Glycols in general are valuable chemical compounds which find a wide variety of utilities. Such compounds are used, for example, as chemical intermediates in the manufacture esters, as well as in the synthesis of polyesters. 1,3-Propanediol, in particular, had been found to be especially useful in a number of applications. 1,3-Propanediol has been prepared by acid-catalyzed hydration of acrolein to form 3-hydroxypropanal which is subsequently hydrogenated to the corresponding glycol. Because of the relatively low reaction rates and product yields obtained, this approach has not led to a viable process for making 1,3-propanediol in large commercial quantities.

The preparation of 1,3-diols, i.e., 1,3-glycols, by the hydroformylation of epoxides, utilizing phosphine-modified cobalt carbonyl complexes as the catalyst, is disclosed in Smith et al U.S. Pat. No. 3,463,819. In particular, this patent shows the production of 1,3-propanediol by hydroformylation of ethylene oxide, using a tertiary hosphine-modified cobalt carbonyl catalyst. very high cobalt-containing catalyst concentrations are needed to provide good yields of 1,3-propanediol.

Lawrence et al U.S. Pat. No. 3,687,981 discloses a process for manufacturing 1,3-propanediol which employs two separate stages. In the first stage, ethylene oxide undergoes a hydroformylation reaction in the presence of a hydroformylation catalyst containing a transition metal, particularly metals of Group VIII of the periodic chart, e.g., cobalt carbonyl tertiary phosphine and rhodium carbonyl, to produce 2-(2 hydroxyethyl)-4-hydroxy-1,3-dioxane. The dioxane compound, together with a small amount of 3-hydroxypropionaldehyde, is separated from the hydroformylation solvent and is catalytically hydrogenated to form 1,3-propanediol.

Smith et al U.S. Pat. No. 3,456,017 discloses production of 1,3-propanediol by hydroformylation of ethylene oxide using, as catalyst, dicobalt hexacarbonyl complexes wherein the remaining two coordination sites of the cobalt moieties are complexed with one or more tertiary phosphine ligands.

Horvitz et al U.S. Pat. No. 4,322,355 discloses the reaction of olefin with aldehyde in the presence of a strong acid catalyst and a co-catalyst selected from antimony and bismuth oxides and salts to provide one, or a mixture of, 1,3-difunctional compounds.

European Patent Publication No. 0257967 discloses a process for producing 1,3-glycols by reacting an epoxide with synthesis gas in an acidic medium in the presence of rhodium and a phosphine. This publication discloses a reaction mixture containing (1) the epoxide; (2) rhodium; (3) a phosphlne; (4) water; (5) carbon monoxide; (6) hydrogen; and (7) an acid. Although a wide range of acid to rhodium molar ratios is disclosed, e.g., from 10/1 to 1/10, this publication discloses a preference for a molar ratio of acid to rhodium of approximately 1. This publication discloses that an induction period, of about 0.5 to 1 hour or more in duration, occurs after the reaction mixture is formed before gas uptake begins. This "induction period", which itself is wasteful because a larger reactor and/or longer time is required to produce a given amount of 1,3-diol, is in part a result of combining some of the epoxide with the rhodium.and phosphine, and possibly other components, to produce the true hydroformylation catalyst. Thus, some of the epoxide is incorporated into the hydroformylation catalyst. Using the epoxide to produce .the catalyst reduces the ultimate yield, of desired products, e.g., 1,3-diol. A rhodium-containing catalyst which does not require an induction period and/or which is made without incorporation of epoxide would clearly be advantageous.

Murphy et al U.S. Pat. No. 4,873,378 discloses substantially the same process as that disclosed in the above-noted European Patent Publication. In addition, this patent discloses that a salt having an alkali metal-cation and a solubilizing anioh is also present in the reaction mixture. This patent discloses that the "induction period" is eliminated in certain examples containing relatively large amounts of alkali metal salts. No salts other than alkali metal salts are suggested.

Murphy et al U.S. Pat. No. 4,873,379 discloses a process for producing 1,3-diols. This patent discloses a reaction mixture containing (1) an epoxide; (2) rhodium; (3) an alkali metal salt promoter; (4) water; (5) carbon monoxide; and (6) hydrogen. No promoters other than alkali metal salts are suggested.

Maher et al U.S. Pat. No. 4,774,361 discloses a solubilized rhodium-phosphite complex catalyzed, liquid recycle hydroformylation process for producing aldehyde by reacting an olefinic unsaturated. compound with carbon monoxide and hydrogen. Billig et al U.S. Pat. Nos. 4,668,651 and 4,769,498 disclose a Group VIII transition metal-poly-phosphite ligand complex catalyst and free poly-phosphite ligand in the production of aldehydes wherein an olefinic compound is reacted with carbon monoxide and hydrogen. Billig et al U.S. Pat. Nos. 4,717,775 and 4,599,206 disclose hydroformylating an olefinically unsaturated organic compound with carbon monoxide and hydrogen in the presence of a rhodium-containing catalyst complexed with a diorganophospite ligand. Billig et al U.S. Pat. No. 4,885,401 discloses hydroformylating an olefinically unsaturated organic compound with carbon monoxide and hydrogen in the presence of a rhodium-containing catalyst complexed with a bis-phosphite ligand. Epoxide hydroformylation is not specifically disclosed in any of these patents. The disclosure of each of the patents identified in this paragraph is incorporated in its entirety by reference herein.

In the article "Aspects of Anionic Rhodium Complex Ligand Effects" by A.S.C. Chan, et al, Journal of Organometallic Chemistry, 279 (1985) 171-179, several anionic rhodium complexes are reported as having been studied as formaldehyde hydroformylation catalysts. various alkali metal-containing crystalline materials, such as [Na(C$_{12}$H$_{24}$O$_6$)][Rh(CO)$_3$(PPh$_3$)] and [K(C$_{12}$H$_{24}$O$_6$)][Rh(CO)$_2$(P(OPh$_3$)$_2$]are reported as having been isolated. No epoxide hydroformylation is suggested.

European Patent Publication No. 0306094 discloses a process for the hydroformylation of certain acrylic acid derivatives in the presence of a homogeneous catalyst system comprising a rhodium compound and one or more triphenylphosphites. No epoxide hydroformylation is suggested.

There continues to be a need for a new epoxide hydroformylation catalyst, and for processes for making and using the same, particularly to produce 1,3-diols and/or 3-hydroxyaldehydes.

SUMMARY OF THE INVENTION

A new epoxide hydroformylation process, a catalyst for use in such process, and process for producing such catalyst have been discovered. The present epoxide hydroformylation process provides high ultimate yields of desired products, such as 1,3-diols and/or 3-hydroxyaldehydes. The present catalytic hydroformylation process provides for high rates of reaction and high selectivity to the desired product or products. Advantageously, less severe hydroformylation reaction conditions and/or reduced catalyst concentrations can be used. Further, the induction period which has been a characteristic of certain of the previously suggested epoxide hydroformylation processes can be reduced in length or even eliminated in the present invention. In addition, the inclusion of one or more of certain promoter components provides enhanced results. In short, the present hydroformylation catalyst compositions and processes provide for substantial benefits, e.g., processing economies and efficiencies, in producing 1,3-diols and/or 3-hydroxyaldehydes.

In one broad aspect, the present invention is directed to a process for producing a 1,3-diol and/or a 3-hydroxyaldehyde. This process comprises contacting a combination of an epoxide, carbon monoxide and hydrogen in the presence of a rhodium-containing catalyst composition effective to promote the hydroformylation of the epoxide at conditions effective to form a 1,3-diol and/or a 3-hydroxyaldehyde. The rhodium-containing catalyst composition comprises an anionic rhodium-containing complex and an electrophile. The product 3-hydroxyaldehyde, if any, is preferably contacted with hydrogen at conditions effective to form a desired 1,3-diol.

The epoxide contacting preferably takes place in the presence of H$^+$ ions in an amount effective to facilitate the epoxide hydroformylation. The anionic rhodium-containing complex preferably includes a phosphorus-containing ligand, more preferably a phosphorus-oxygen-containing ligand, in particular at least one phosphite ligand. In one useful embodiment, the catalyst composition includes a cation other than H$^+$ and preferably other than an alkali metal cation, in particular an organo-containing cation. A promoter component is preferably included to enhance the rate of epoxide hydroformylation and/or the selectivity to 1,3-diol and/or 3-hydroxyaldehyde.

Another broad aspect of the present invention involves a composition which comprises a liquid medium, an anionic rhodium-containing complex including a ligand containing phosphorus and oxygen; H$^+$ other than by being covalently bonded to the complex; and a cation other than H$^+$. This composition has catalytic activity for promoting the hydroformylation of an epoxide. A promoter component is preferably included and is effective to enhance the rate and/or selectivity. of the epoxide hydroformylation reaction.

In addition, another composition useful as an epoxide hydroformylation catalyst is provided. This composition comprises a liquid medium, a rhodium-containing complex including a ligand containing phosphorus and oxygen; an ionic component having sufficient basicity to render the complex anionic and including a cation other than H$^+$; and H$^+$. The composition has catalytic activity to promote the hydroformylation of an epoxide. A promoter component is preferably included and is effective to enhance the rate and/or selectivity of the epoxide hydroformylation reaction.

In a further broad aspect, the present invention is directed to a process for producing rhodium-containing compositions, e.g., epoxide hydroformylation catalyst compositions. This process comprises contacting, preferably in a liquid medium, a rhodium source, a ligand source and an ionic component, preferably an ionic component including an organo-containing cation, and preferably an acid, at conditions effective to produce an anionic rhodium-containing complex including a ligand containing phosphorus and oxygen. This rhodium-containing composition, in particular the anionic rhodium-containing complex, has activity to promote the hydroformylation of an epoxide.

These and other aspects and advantages of the present invention are set forth in the following detailed description, examples and claims.

DETAILED DESCRIPTION OF THE INVENTION

The process of the present invention provides a method for the manufacture of 1,3-diols or 3-hydroxyaldehydes, which are precursors of 1,3-diols, through the hydroformylation of epoxides. The desired 1,3-diols and 3-hydroxyaldehydes, in their monomeric forms, therefore contain one more carbon atom and one more oxygen atom than the epoxide. Thus, for example, when the epoxide reactant is ethylene oxide, containing 2 carbon atoms and one oxygen atom, the product 1,3-diol is 1,3-propanediol and the product 3-hydroxyaldehyde is 3-hydroxypropionaldehyde, each of which contains 3 carbon atoms and two oxygen atoms. As used herein, the terms "1,3-diol" and "3-hydroxyaldehyde" refer not only to the monomeric forms of these compounds, but also to oligomeric forms, e.g., in which the degree of polymerization is up to about 10, in particular dimers, trimers and tetramers. Mixed oligomers of 1,3-diols and 3-hydroxyaldehydes are also possible and are included within the scope of such terms.

The suitable epoxides have the general formula

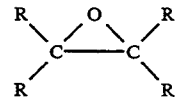

wherein each R is selected from hydrogen, monovalent aliphatic or aromatic groups containing 1 to about 12 carbon atoms, divalent aliphatic groups containing 4 to about 6 carbon atoms and a bond with another R which is divalent. For example, when one R is a divalent saturated aliphatic group having 4 carbon atoms and one R bonded to each of the carbon atoms in the above formula is hydrogen, then the epoxide is cyclohexene oxide. Examples of specific epoxides which are useful in the present invention include ethylene oxide, propylene oxide, 1,2-epoxyoctane, cyclohexene oxide, and styrene oxide. The epoxide may be present during, particularly at the start of, the hydroformylation step of the present invention in widely varying amounts, for example, at a concentration in the range of about 0.01% to about 95%, preferably about 0.5% to about 75%, by weight based on the total weight of reactants, catalyst and liquid medium present during this step.

The hydroformylation contacting or step takes place in the presence of, e.g., in, a suitable liquid medium, which is preferably a solvent for the epoxide and rhodium-containing catalyst composition. Among the suitable liquid media are aliphatic hydrocarbon components, aromatic hydrocarbon components, including benzene, toluene, xylenes and the like, ethers, including high molecular weight ethers, polyethers, especially glycol polyethers, and cyclic ethers, amides, sulfones, alcohols, ketones, esters and mixtures thereof. Specific examples of suitable liquid media include glyme (dimethoxyethane), diglyme, tetraglyme (the dimethyl ether of tetraethylene glycol), tetrahydrofuran, and oils, e.g., such as those sold under the trademark UCO ™ by Union Carbide Corporation, which comprise mixed glycol polyethers of ethylene and propylene glycol subunits.

The liquid medium preferably solubilizes the catalyst and the epoxide reactant. Preferred liquid media do not substantially react with any of the other components present during the hydroformylation contacting. In polar liquid media many of the components of the present catalyst compositions are often present as individual charged species, e.g., complexes, ions and the like. In non-polar liquid media these components are often present as ion pairs. Such components are referred to herein, regardless of the type of liquid medium being employed, as individual charged species, it being understood that one or more of such components may not be present as such, e.g., may be present in an ion pair. For lower molecular weight epoxides, e.g., ethylene oxide, liquid media such as glyme, tetraglyme, tetrahydrofuran, and the like and mixtures thereof are useful. For higher molecular weight epoxides, petroleum ethers and hydrocarbon materials such as benzene, toluene and xylenes, may be appropriate.

An important preferred feature of the present invention is the use of liquid media for hydroformylation of epoxides, particularly low molecular weight epoxides such as those containing 2 to about 5 carbon atoms, especially ethylene oxide, in which the product 1,3-diol and/or 3-hydroxyaldehyde is insoluble or immiscible over a useful range of conditions. In particular, the present catalysts have substantial activity and selectivity for 1,3-diols and/or 3-hydroxyaldehydes in the hydroformylation of lower molecular weight epoxides using liquid media which heretofore have been less suited to such hydroformylation service. Such liquid media, in particular hydrocarbons and mixtures thereof, especially aromatic hydrocarbons and mixtures thereof, are not only effective in the epoxide hydroformylation step, but also form a two phase mixture with the product 1,3-diol and/or 35 hydroxyaldehyde, in particular the 3-hydroxyaldehyde, at conditions so that the product or products can be separated from the liquid medium, e.g., using conventional phase separation techniques, such as centrifugation, decantation and the like.

Thus, in one embodiment, the present 1,3-diol/3-hydroxyaldehyde production process includes a step or steps in which the reaction mixture, after hydroformylation, in particular the liquid medium and the product 3-hydroxyaldehyde, are caused to form a liquid medium-rich phase and a 3-hydroxyaldehyde-rich phase. In one particularly useful embodiment, the reaction mixture is cooled from hydroformylation reaction temperature to provide for the recovery of such phases. For example, cooling or maintaining the reaction mixture at a temperature in the range of about $-50°$ C. to about $50°$ C. sometimes causes the desired phase formation. Care should be taken to avoid temperatures at which a significant amount of the liquid medium solidifies. The liquid medium-rich phase has a higher concentration of liquid medium, and preferably a higher concentration of catalyst composition components, than that present in the total liquid reaction mixture and product 3-hydroxyaldehyde after hydroformylation. Analogously, the 3-hydroxyaldehyde-rich phase has a higher concentration of 3-hydroxyaldehyde than that present in the total or combined liquid reaction mixture and product 3-hydroxyaldehyde after hydroformylation.

The liquid medium-rich phase and the 3-hydroxyaldehyde-rich phase, which are in contact with each other, are preferably-separated, e.g., using conventional phase separation techniques, to form a separated 3-hydroxyaldehyde-rich material. This separated hydroxyaldehyde-rich material, which includes a minor amount of other materials, such as the liquid medium and possibly the 1,3-diol and other components present in the reaction mixture, is preferably further processed to produce the desired 1,3-diol. The separated 3-hydroxyaldehyde-rich material can be used directly in the hydrogenation step to produce 1,3-diol. This "direct" hydrogenation is particularly useful when the liquid medium included with the 3-hydroxyaldehyde-rich material is selected from hydrocarbons, in particular aromatic hydrocarbons, such as benzene, toluene and xylenes. Such liquid medium materials do not substantially detrimentally affect the hydrogenation step. After the hydrogenation, the product 1,3-diol can be separated, e.g., using conventional separation techniques, to produce the final 1,3-diol product of desired purity. If desired, the separated liquid medium-rich material can be recycled for further use in the hydroformylation step.

The rhodium source which is employed to make the present catalyst composition may be in the form of rhodium metal, rhodium salts, and/or rhodium complexes. Among the rhodium sources useful in the practice of the present invention are those selected from one or more of rhodium metal, rhodium oxides, $RhI_3$, $RhBr_3$, $RhCl_3$, $Rh(acac)_3$, $Rh(CO)_2acac$, $Rh_4(CO)_{12}$, $Rh_6(CO)_{16}$, $[RhCl(CO)_2]_2$ and $Rh(NO_3)_3$, wherein acac represents acetylacetonate. Rhodium may be used as a pre-formed anion, as for example $Rh_6(CO)15^{2-}$ and other similar anionic rhodium cluster salts.

The concentration of rhodium in the hydroformylation contacting may vary depending, for example, on the specific epoxide and liquid medium being employed and/or on the contacting conditions. Such concentration is preferably in the range of about 100 ppm to about 10,000 ppm by weight, calculated as elemental rhodium, based on the total weight of liquid medium and epoxide present during the hydroformylation.

The term "complex" as used herein and in the claims means a coordination compound formed by the union of one or more electronically rich molecules or atoms capable of independent existence with one or more electronically poor molecules or atoms, each of which is also capable of independent existence. For example, the phosphite ligands employable herein include at least one phosphorus donor atom, having one available or unshared pair of electrons and thus are capable of forming a coordinate bond with rhodium. Carbon monoxide (which is also properly classified as a ligand) is also present and complexed with rhodium. The ultimate composition of the anionic rhodium-containing complex may also contain an additional ligand, e.g., hydrogen or an anion satisfying the coordination sites or nuclear charge of rhodium. Illustrative additional ligands include, e.g., halogen ($Cl^-$, $Br^-$, $I^-$), alkyl, aryl, substituted aryl, $CF_3^-$, $-C_2F_5$, $CN^-$, $R'_3PO$ and $R'P(O)(OH)O$ (wherein each $R'$ is alkyl or aryl), acetate, acetylacetonate, $SO_4^=$, $PF_6^-$, $NO_2^-$, $NO_3^-$, $CH_3O^-$, $CH_2=CHCH_2^-$, $C_6H_5CN$, $CH_3CN$, $NO$, $NH_3$, pyridine, $(C_2H_5)_3N$, mono-olefins, diolefins and triolefins, tetrahydrofuran and the like. It is of course to be understood that the anionic rhodium-containing complex species is preferably free of any additional organic ligand or anion that might poison the catalyst composition and have an undue adverse effect on catalyst composition performance. For instance, it is known that in conventional rhodium catalyzed hydroformylation reactions that halogen anions and sulfur compounds can poison the catalyst. Accordingly it is preferred that the complexes also be free of halogen and sulfur directly bonded to the rhodium, although such may not be absolutely necessary.

Thus the anionic rhodium-containing complex species in its simplest form preferably contains an amount of ligand other than carbon monoxide, more preferably a phosphorus-containing ligand and still more preferably a phosphorus and oxygen-containing ligand, in particular a phosphite ligand, and carbon monoxide equal to a total of two (2), three (3) or four (4) moles in complex combination with one mole of rhodium. Thus, the anionic rhodium-containing complex may comprise a complex mixture, in monomeric, dimeric or higher nuclearity forms, which are characterized by at least one ligand molecule other than carbon monoxide complexed per one atom of rhodium. Carbon monoxide may be, and preferably is, also present and complexed with the rhodium in the anionic rhodium-containing complex species.

The anionic rhodium-containing complex can be preformed prior to introduction into the hydroformylation reaction zone or the anionic rhodium-containing complex can be prepared in situ during the hydroformylation. Such preforming or preparing preferably occurs in the presence of free ligand other than carbon monoxide, although such may not be absolutely necessary.

Any suitable ligand other than or in addition to carbon monoxide may be employed in the present anionic rhodium-containing complexes. Of course, such ligand should have no substantial detrimental effect on the catalytic activity of the catalyst composition or on the epoxide hydroformylation process in general. Phosphorous-containing ligands are preferred, with phosphorus and oxygen-containing ligands being more preferred, in particular phosphite ligands. The present anionic rhodium-containing complexes preferably have substantial stability at the conditions of the epoxide hydroformylation step. Thus, in one embodiment, the anionic rhodium-containing complex is preferably such that at least about 50% of the complex remains after 2 hours, more preferably after 5 hours and still more preferably after 10 hours, at epoxide hydroformylation conditions, for example at reference epoxide hydroformylation conditions. As used herein, reference epoxide hydroformylation conditions are as follows:

| Epoxide | ethylene oxide |
|---|---|
| Liquid medium | glyme |
| Initial weight ratio of epoxide to liquid medium | 0.125 |
| $CO/H_2$ (molar) | 1:2 |
| Pressure | 1000 psig |
| Temperature | 110° C. |
| Rhodium concentration | 2000 ppm (by weight) |

Certain materials, such as certain phosphines, have been found to be unstable at such conditions, e.g., forming phosphonium ions from the phosphine and epoxide present at such conditions.

As noted above, more preferably the ligands contain both oxygen and phosphorus. Examples of such ligands include phosphonites, phosphinites and phosphites.

The phosphonites useful in the present invention preferably have the general. formula

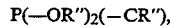
P(—OR")₂(—CR"), while the presently useful phosphinites preferably have the general formula

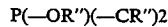
P(—OR")(—CR")₂ wherein each R" is independently selected from organic radicals, e.g., hydrocarbyl ( or hydrocarbon ) radicals and substituted hydrocarbyl radicals, such as those described elsewhere herein.

Illustrative organophosphite ligands that may be employed in this invention include diorganophosphites having the formula

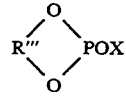

wherein R'" represents a divalent organic radical and X represents a monovalent hydrocarbon radical, e.g., as defined in detail below.

Representative divalent radicals represented by R'" include those wherein R'" may be a divalent acyclic radical or a divalent aromatic radical. Illustrative divalent acyclic radicals include alkylene, alkylene-oxy-alkylene, alkylene-NX'-alkylene wherein X' is hydrogen or a monovalent hydrocarbon radical, alkylene-S-alkylene, and cycloalkylene radicals; and the like, such as disclosed more fully e.g. in U.S. Pat. Nos. 3,415,906 and 4,567,306, and the like, the entire disclosures of which are incorporated by reference herein. Illustrative divalent aromatic radicals include arylene, bi-arylene, arylene-alkylene, arylene, alkylene-arylene, arylene-oxy-arylene, arylene-NX'-arylene and arylene—NX'-alkylene wherein X' is hydrogen or a monovalent hydrocarbon radical, arylene-S-alkylene, and arylene-S-arylene radicals; and the like. More preferably R'" is a divalent aromatic radical.

Among the phosphite ligands employable in this invention are those having the general formula

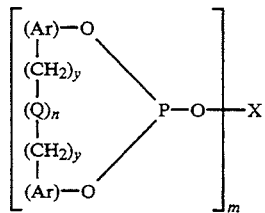

wherein each Ar group represents an identical or different substituted or unsubstituted aryl radical; X represents a monovalent hydrocarbyl or hydrocarbon radical when m is 1, and, when m is other than 1, a m-valent radical selected from the group consisting of alkylene, alkylene-oxy-alkylene, arylene, and arylene-(CH2)y-(Q)n(CH2)y-arylene, with each arylene radical representing an identical or different, substituted or unsubstituted arylene radical; each y individually has a value of 0 or 1; each Q individually represents a divalent bridging group selected from the group consisting of —$CR^1R^2$—, —O—, —S—, —$NR^{3-1}$, —$SiR^4R^{5-1}$ and —CO—, wherein each $R^1$ and $R^2$ radical individually represents a radical selected from the group consisting of hydrogen, alkyl containing 1 to about 12 carbon atoms, phenyl, tolyl and anisyl, and each $R^3$, $R^4$, and $R^5$ radical individually represents hydrogen or methyl; each n individually has a value of 0 or 1; and m has a value of 1 to 6, preferably 1 to 4. In one embodiment, each y and each n has a value of 0. When either n is 1, its corresponding Q is preferably a $CR^1R^2$ bridging group as defined above and more preferably methylene (—$CH_2$—) or alkylidene (—$CHR^2$—) with $R^2$ being an alkyl radical containing 1 to about 12 carbon atoms, (e.g., methyl, ethyl, propyl, isopropyl, butyl, isodecyl, dodecyl, etc., especially methyl).

Illustrative monovalent hydrocarbon radicals represented by X when m is 1 in the above formula include substituted or unsubstituted monovalent hydrocarbon radicals containing 1 to about 30 carbon atoms selected from the group consisting of substituted or unsubstituted alkyl, aryl, alkaryl, aralkyl and alicyclic radicals. When m is 1, X preferably represents a substituted or unsubstituted radical selected from the group consisting of alkyl and aryl radicals.

More specific illustrative monovalent hydrocarbon radicals represented by X include primary, secondary and tertiary alkyl radicals such as methyl, ethyl, n-propyl, isopropyl, butyl, sec-butyl, t-butyl, t-butylethyl, t-butylpropyl, n-hexyl, amyl, sec-amyl, t-amyl, iso-octyl, 2-ethylhexyl, decyl, octadecyl and the like; aryl radicals, such as phenyl, naphthyl, anthracyl, and the like; aralkyl radicals, such as benzyl, phenylethyl, and the like, alkaryl radicals, such as tolyl, xylyl, and the like; and alicyclic radicals, such as cyclopentyl, cyclohexyl, cyclooctyl, cyclohexylethyl, and the like. Preferably the unsubstituted alkyl radicals may contain about 1 to about 18 carbon atoms, more preferably 1 to about 10 carbon atoms, while the unsubstituted aryl, aralkyl, alkaryl and alicyclic radicals preferably from 6 to about 18 carbon atoms.

Illustrative m-valent radicals represented by X when m is other than 1 in the above formula include substituted and unsubstituted radicals selected from the group consisting of alkylene, alkylene-oxy-alkylene, phenylene, naphthylene, phenylene-(CH2)y-(Q)n-(CH2)-phenylene and naphthylene-(CH2)y(Q)m(CH2)y-naphthylene-radicals,with Q, n and y are the same as defined above. More specific illustrative m-valent radicals represented by X when m is other than 1 include straight or branched chain alkylene radicals such as —(CH2)x— wherein x has a value of 2 to about 18 (preferably 2 to about 12), pentaerythritol, 1,2,6-hexylene and the like; —CH2CH2OCH2CH2—, 1,4-phenylene, 2,3-phenylene, 1,3,5-phenylene, 1,3-phenylene, 1,4-naphthylene, 1,5-naphthylene, 1,8-naphthylene, 2,3-naphthylene, 1,5-naphthylene, 1,8-naphthylene, 2,3-naphthylene, 1,1'-bipheny-2,2'-diyl, 2,2'-biphenyl-1,1'-diyl, 1,1'-biphenyl-4,4'-diyl, 1,1'-binaphthyl-2,2'-diyl, 2,2'naphthyl-1,1'-diyl, phenylene-CH2-phenylene, phenylene-S-phenylene, CH2-phenylene-CH2, phenylene —CH(CH3)-phenylene radicals and the like.

Thus, when m is other than 1, X is a m-valent radical which may contain 2 to about 30 carbon atoms, wherein the alkylene and alkylene-oxy-alkylene radicals preferably contain 2 to about 18 and more preferably 2 to about 12 carbon atoms, while the arylene type radicals may contain 6 to about 18 carbon atoms. In this embodiment, X is preferably ethylene or an arylene type radical and more preferably a naphthylene or a substituted or unsubstituted phenylene-(Q)n-phenylene radical.

Illustrative aryl radicals represented by the Ar groups and the arylene radicals of X in the above formula include both substituted and unsubstituted aryl radicals. Such aryl radicals preferably contain 6 to about 18 carbon atoms such as phenylene ($C_6H_4$),naphthylene ($C_{10}H_6$),anthracylene ($C_{14}H_8$) and the like.

Illustrative substituent groups that may be present on the alkylene or arylene radicals of X and the aryl groups represented by Ar in the above formula include monovalent hydrocarbon radicals such as substituted or unsubstituted alkyl, aryl, alkaryl, aralkyl and alicyclic radicals as well as silyl radicals such as —$Si(R^6)_3$ and —$Si(OR^6)_3$, amino radicals such as —$N(R^6)_2$, acyl radicals such as —$C(O)R^6$, carbonyloxy radicals such as —$C(O)OR^6$ oxycarbonyl radicals such as —$OC(O)R^6$ amido radicals such as —$C(O)N(R^6)_2$ and —$N(R^6)$-$C(O)R^6$, sulfonyl radicals such as —$S$—$(O)_2R^6$, sulfinyl radicals such as —$S(O)R^6$ ether (e.g. alkoxy) radicals such as —$OR^6$ thionyl ether radicals such as —$SR^6$, phosphonyl radicals such as —$P(O)(R^6)_2$, and halogen, nitro, cyano, trifluoromethyl and hydroxy radicals, and the like, wherein each $R^6$ individually represents the same or different, substituted or unsubstituted monovalent hydrocarbon radical as defined elsewhere herein with the proviso that in amino substituents such as —$N(R^6)_2$,each $R^6$ taken together can also represent a divalent bridging group that forms a heterocyclic radical with the nitrogen atom and in amino and amido substituents such as —$N(R^6)_2$, —$C(O)N(R^6)_2$ and —$N(R^6)C(O)R^6$, each —$R^6$ bonded to N can also be hydrogen, while in phosphonyl substituents such as —$P(O)(R^6)_2$, one $R^6$ can also be hydrogen. Preferably the monovalent hydrocarbon substituent radicals, including those represented by $R^6$, are unsubstituted alkyl or aryl radicals, although if desired they in turn may be substituted with any substituent which does not unduly adversely affect the processes or compositions of this invention, such as, for example, those hydrocarbon and non-hydrocarbon substituent radicals herein outlined.

Among the more specific unsubstituted monovalent hydrocarbon substituent radicals, including those represented by $R^6$, that may be bonded to the alkylene and-/or the arylene radicals of X and/or the Ar groups of the above formula that may be mentioned are alkyl radicals including primary, secondary and tertiary alkyl radicals such as methyl, ethyl, n-propyl, isopropyl, butyl, sec-butyl, t-butyl, neo-pentyl, n-hexyl, amyl, sec-amyl, t-amyl, iso-octyl, decyl, and the like; aryl radicals such as phenyl, naphthyl and the like; aralkyl radicals such as benzyl, phenylethyl, triphenylmethyl, and the like; alkaryl radicals such as tolyl, xylyl, and the like; and alicyclic radicals such as cyclopentyl, cyclohexyl, 1-methylcyclohexyl, cyclooctyl, cyclohexylethyl, and the like. More specific illustrative non-hydrocarbon substituents that may be present on the alkylene and/or the arylene radicals of X and/or the Ar groups of the above formula include e.g., halogen, preferably chlorine or fluorine, $-NO_2$, $-CN$, $-CF_3$, $-OH$, $-Si(CH_3)_3$, $-Si(OCH_3)_3$, $-Si(C_3H_7)_3$, $-C(O)CH_3$, $-C(O)C_2H_5$, $-OC(O)C_6H_5$, $-C(O)OCH_3$, $-N(CH_3)_2$, $-NH_2$, $-NHCH_3$, $-NH(C_2H_5)$, $-CONH_2$, $-CON(CH_3)_2$, $-S(O)_2C_2H_5$, $-OCH_3$, $-OC_2H_5$, $-OC_6H_5$, $-C-(O)C_6H_5$, $-O(t-C_4H_9)$, $-SC_2H_5$, $-(OCH_2CH_2)_3OCH_3$, $-(OCH_2CH_2)_2OCH_3$, $-(OCH_2CH_2)OCH_3$, $-SCH_3$, $-S(O)CH_3$, $-SC_6H_5$, $-P(O)(C_6H_5)_2$, $-P(O)(CH_3)_2$, $-P(O)(C_2H_5)_2$, $-P(O)(C_3H_7)_2$, $-P(O)(C_4H_9)_2$, $-P-(O)(C_6H_{13})_2$, $-P(O)CH_3(C_6H_5)$, $-P(O)(H)(C_6H_5)$, $-NHC(O)CH_3$, and the like. The substituent radicals present on the alkylene and/or arylene radicals of X and/or the Ar groups of the above formula may also contain 1 to about 18 carbon atoms and may be bonded to the alkylene and/or arylene radicals of X and/or the Ar groups in any suitable position as may be the bridging group $-(CH_2)_y-(Q)_n-(CH_2)_y-$ connecting the two Ar groups or the two arylene groups of X in the above formula. Moreover, each Ar radical and/or alkylene and/or arylene radical of X may contain one or more substituent groups which substituent groups may also be the same or different in any given phosphite. Preferred substituent radicals include alkyl and alkoxy radicals containing 1 to about 18 carbon atoms and more preferably 1 to about 10 carbon atoms, especially t-butyl and methoxy.

Among the more preferred phosphite ligands are those wherein the two Ar groups linked by the bridging group represented by $-(CH_2)_y-(Q)_n-(CH_2)_y-$ in the above formula are bonded through their ortho positions in relation to the oxygen atoms that connect the Ar groups to the phosphorus atom. It is also preferred that any substituent radical, when present on such Ar groups be bonded in the para and/or ortho position of the aryl in relation to the oxygen atom that bonds the given substituted Ar group to its phosphorus atom.

In one embodiment, the phosphite ligands employable in this invention are those of the formulas

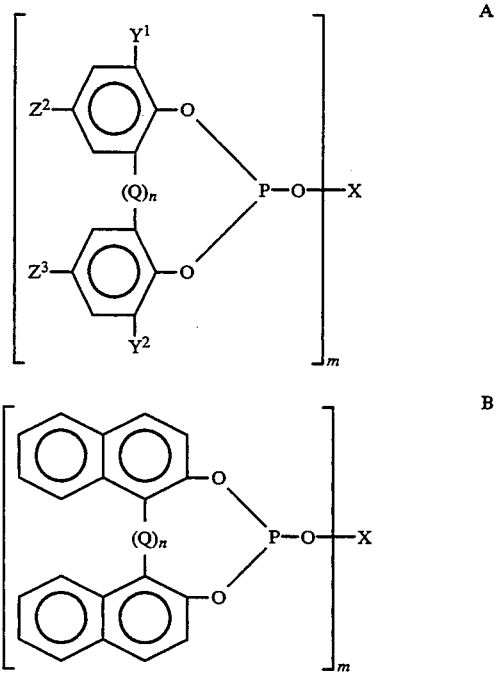

wherein in said Formulas (A) and (B), Q is $-CR^1R^2$ wherein each $R^1$ and $R^2$ radical individually represents a radical selected from the group consisting of hydrogen, alkyl containing 1 to about 12 carbon atoms (e.g. methyl, propyl, isopropyl, butyl, isodecyl, dodecyl, etc.) phenyl, tolyl and anisyl, and n has a value of 0 to 1; each $y^1$, $y^2$, $Z^2$ and $Z^3$ group individually represents a radical selected from the group consisting of hydrogen, an alkyl radical containing 1 to about 18 carbon atoms, substituted or unsubstituted aryl, alkaryl, aralkyl and alicyclic radicals as defined and exemplified herein above (e.g. phenyl, benzyl, cyclohexyl, 1-methylcyclohexyl, and the like), cyano, halogen, nitro, trifluoromethyl, hydroxy, as well as the carbonyloxy, amino, acyl, phosphonyl, oxycarbonyl, amido, sulfinyl, sulfonyl, silyl, alkoxy, and thionyl as defined and exemplified herein above, and m has a value of 2 to 6, more preferably 2 to 4 and still more preferably 2. Preferably both $y^1$ and $y^2$ are radicals having a steric hindrance of isopropyl, or more preferably t-butyl, or greater. Preferably Q represents a methylene ($-CH_2-$)bridging group or an alkylidene ($-CH-R^2-$) bridging group wherein $R^2$ is an alkyl radical containing 1 to about 12 carbon atoms, especially methyl. The more preferred ligands are those of Formula (A) above, wherein both $y^1$ and $y^2$ are branched chain alkyl radicals having three to five carbon atoms, especially t-butyl, and $Z^2$ and $Z^3$ are hydrogen, an alkyl radical, especially t-butyl, a hydroxy radical or an alkoxy radical, especially methoxy.

Further preferred phosphite ligands include those wherein X in the above phosphite formulas is a divalent radical selected from the group consisting of alkylene, especially ethylene, alkylene-oxy-alkylene, especially $-CH_2CH_2OCH_2CH_2-$, and substituted or unsubstituted phenylene, naphthylene, naphthylene $-(Q)_n-$naphthylene and phenylene $-(Q-)_n$-phenylene radicals wherein Q and n are the same as both generically and preferably defined herein. Among the more preferred bisphosphite type ligands when m is 2 are those wherein X is a divalent radical selected from the group consisting of 1,2-ethylene, naphthylene, substituted phenylene and substituted phenylene —(Q-)n -phenylene radicals, especially 1,4-naphthylene and 1,5-naphthylene. Moreover the preferred substituents on such phenylene and/or phenylene —(Q)n-phenylene radicals are preferably radicals selected from the group consisting of alkyl and alkoxy radicals, which most preferably correspond to the substituent radicals of $y^1$, $y^2$, $Z^2$ and $Z^3$ defined herein.

Accordingly, another preferred class of bis-phosphite ligands employable herein are those of the formulas

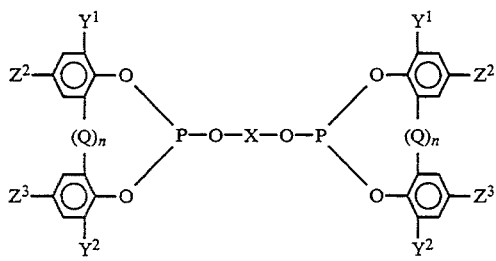

C and

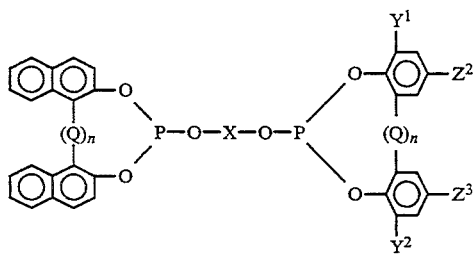

D wherein in said Formula (C) and (D), each $y^1$, $y^2$, Q, X, $Z^2$, $Z^3$ and n are the same as generically and preferably defined in Formulas (A) and (B) above and still more preferably n is zero. Of course it is to be understood that each $y^1$, $yl^2$, Q, $Z^2$, $Z^3$ and n can be the same or different in any given phosphite. More preferably each $y^1$, $y^2$, $Z^2$ and $Z^3$ group individually represents a radical selected from the group consisting of hydrogen, an alkyl radical containing 1 to about 8 carbon atoms, substituted or unsubstituted aryl, alkaryl, aralkyl and alicyclic radicals as defined and exemplified herein above (e.g. phenyl, benzyl, cyclohexyl, 1-methylcyclohexyl, and the like), cyano, halogen, nitro, trifluoromethyl, hydroxy, as well as the carbonyloxy, amino, acyl, phosphonyl, oxycarbonyl, amido, sulfinyl, sulfonyl, silyl, alkoxy, and thionyl radicals as defined and exemplified herein.

Preferably both $y^1$ and $y^2$ are radicals having a steric hindrance of isopropyl, or more preferably t-butyl, or greater. The more preferred ligands are those of above, wherein both $y^1$ and $y^2$ are branched chain alkyl radicals having three to five carbon atoms, especially t-butyl, and $Z^2$ and $Z^3$ are hydrogen, an alkyl radical especially t-butyl, a hydroxy radical or an alkoxy radicals especially methoxy.

Still another group of phosphites that may be employed in this invention are tertiary organopolyphosphites. Such phosphites may contain two or more of such tertiary (trivalent) phosphorus atoms such as those of the formula

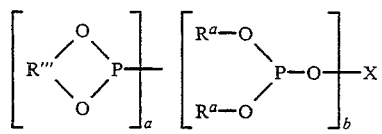

wherein X represents a substituted or unsubstituted m-valent hydrocarbon radical, R''' is the same as defined elsewhere herein, each $R^a$ is independently a substituted or unsubstituted monovalent hydrocarbon radical, a and b can each have a value of 0 to 6 with the proviso that the sum of a +b is 2 to 6 and m equals a +b. Illustrative tertiary organopolyphosphites may include bisphosphites such as those of the formulas

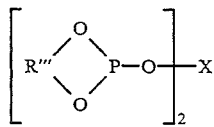

wherein R''' is a divalent organic radical as defined elsewhere herein, and X is a substituted or unsubstituted divalent hydrocarbon radical; and

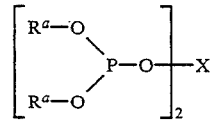

wherein each $R^a$ is independently a substituted or unsubstituted monovalent hydrocarbon radical, and x is a substituted or unsubstituted divalent hydrocarbon radical; and

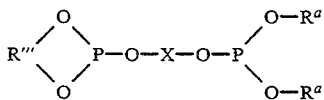

wherein R''' is a divalent organic radical as defined elsewhere herein, each $R^a$ is independently a substituted or unsubstituted monovalent hydrocarbon radical, and x is a substituted or unsubstituted divalent hydrocarbon radical.

Representative of yet another class of bisphosphites that may be employed in this invention are those in which the

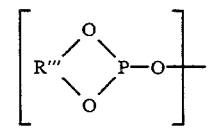

of the above formula is replaced by

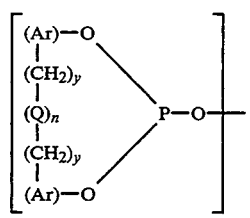

wherein each Ar group, and X and Q group are as defined elsewhere in a corresponding context.

Another group of phosphites that may be employed in this invention are those of the formula

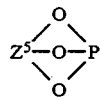

wherein $Z^5$ represents a trivalent organic radical, such as described in greater detail e.g. in the above-referenced U.S. Pat. No. 4,567,306.

Finally, another group of phosphites that may be employed in this invention include triorganophosphites, such as tris(ortho-phenyl)-phenyl phosphite, tris (ortho-methyl)phenyl phosphite, tris (ortho-t-butyl)-phenyl phosphite and the like.

Thus the phosphite ligand employable in this invention may be a tertiary organic phosphite ligand selected from the group consisting of monoorganophosphites, diorganophosphites, triorganophosphites, and organopolyphosphites, such as described above.

Additional illustrative examples of the phosphite ligands useful in this invention include.

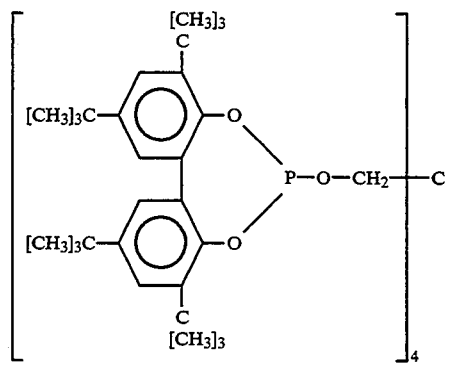

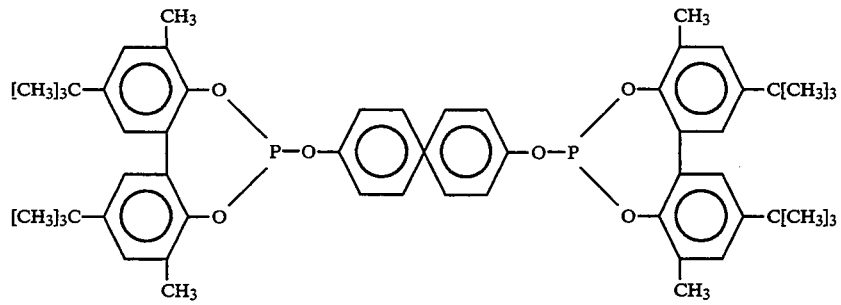

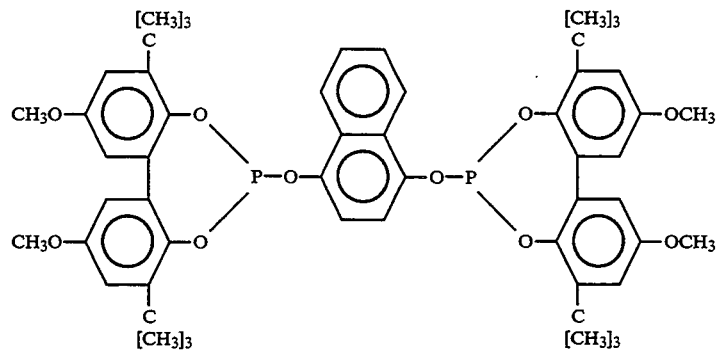

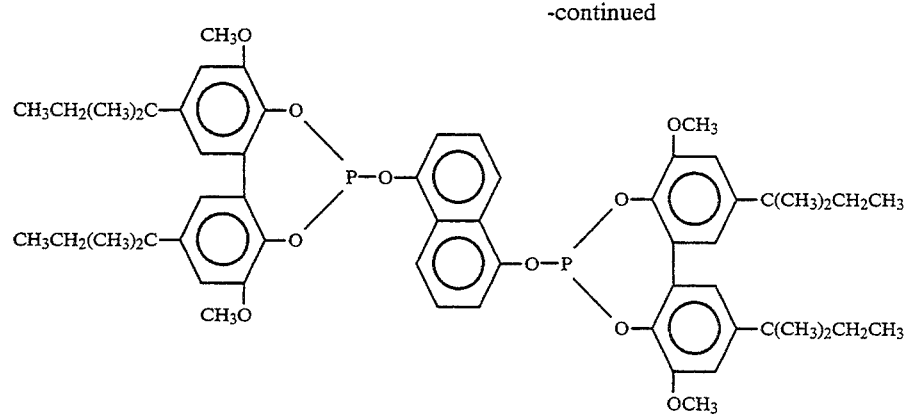
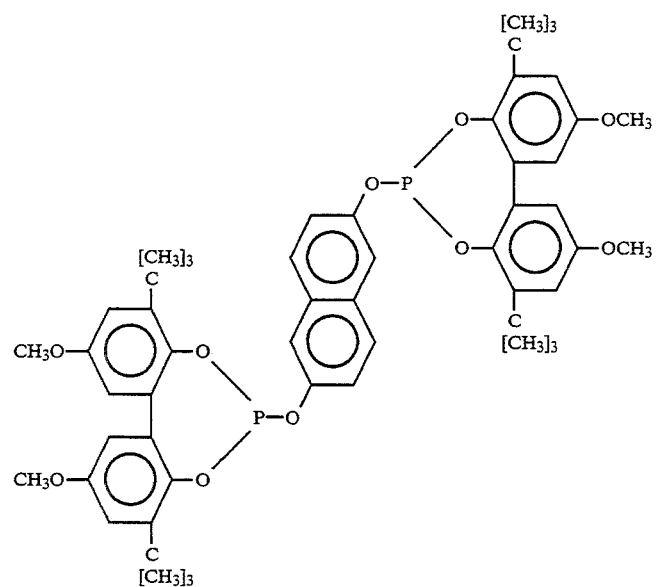
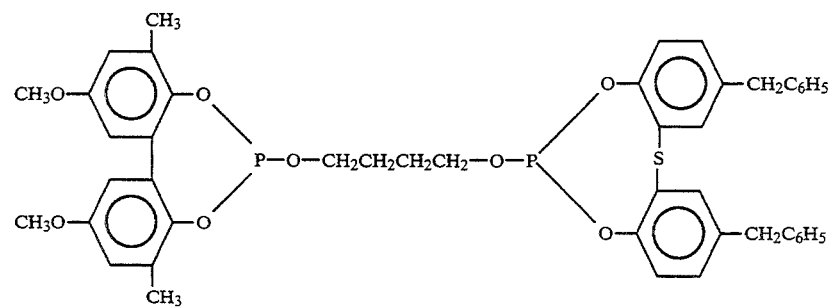
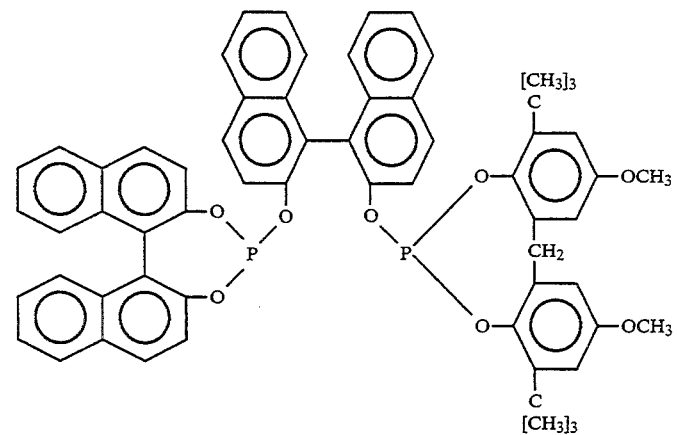

-continued
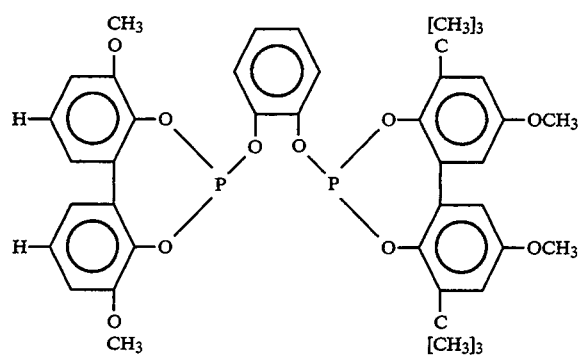
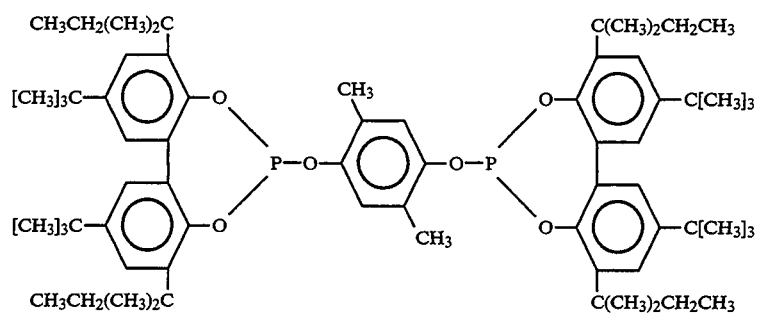
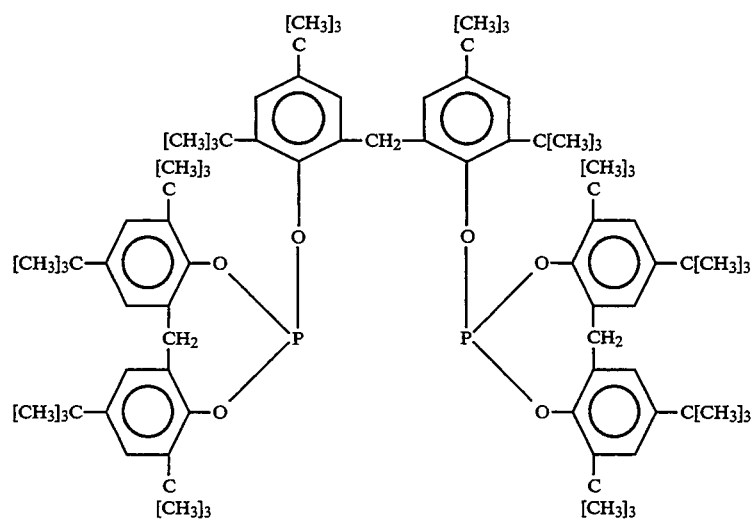
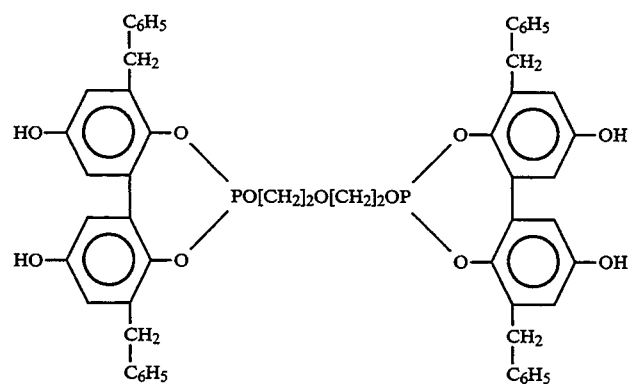

-continued
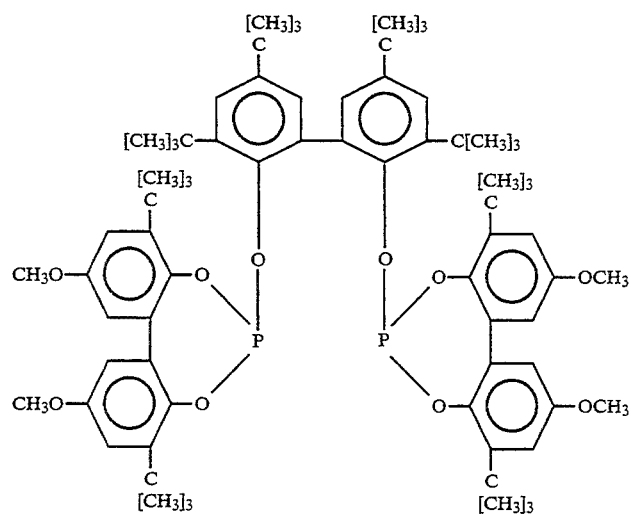
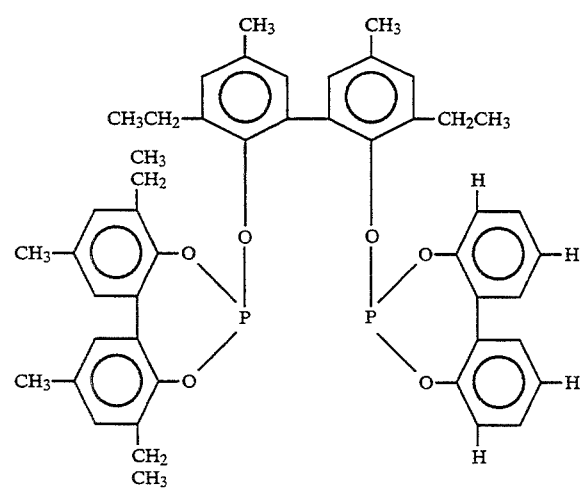
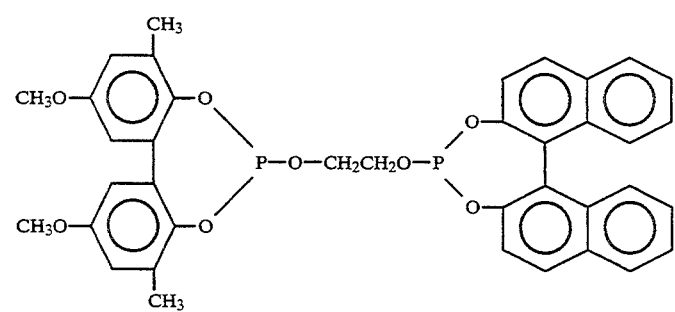

-continued
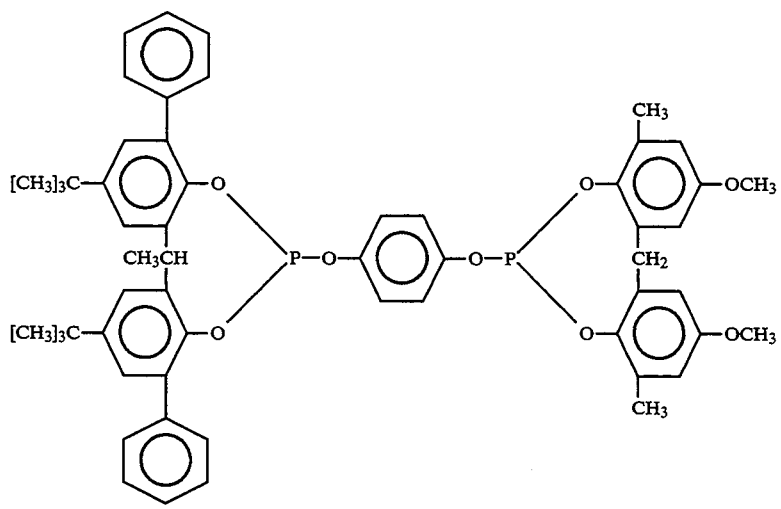
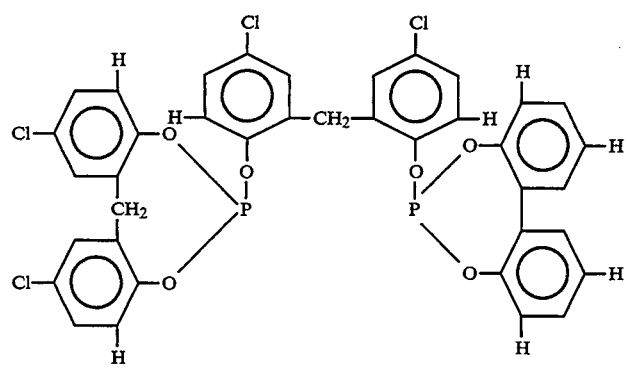
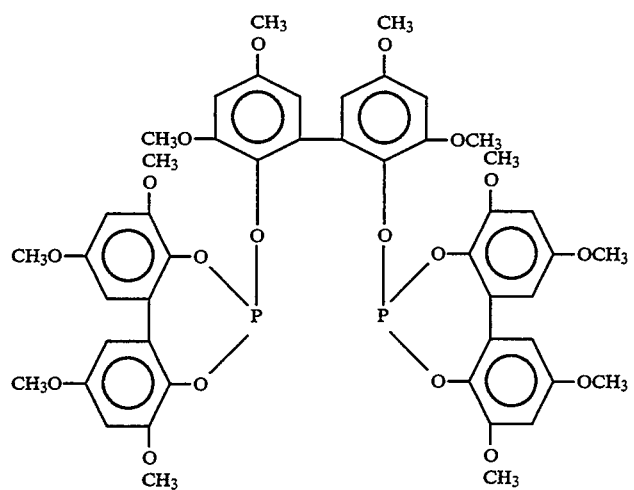

-continued
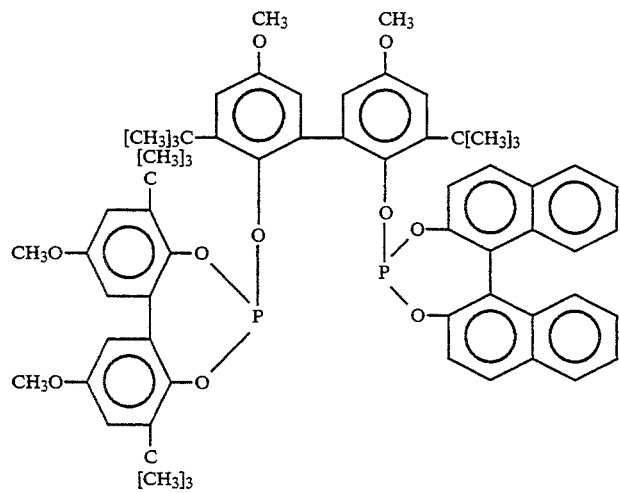
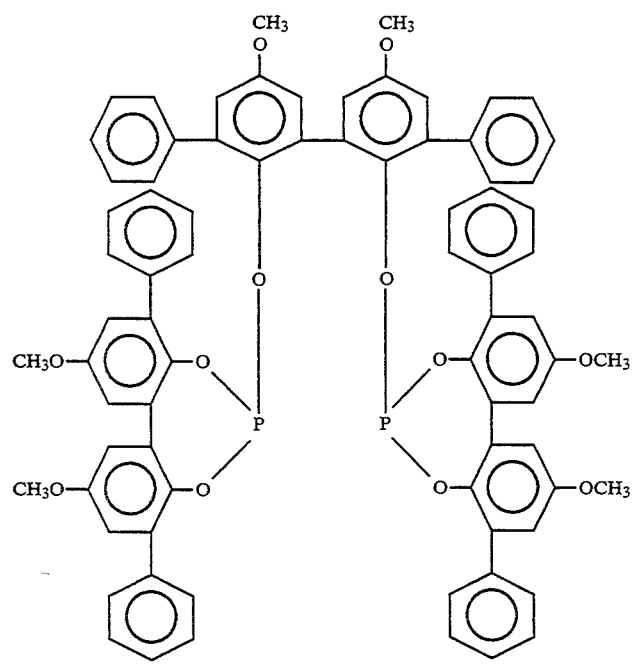
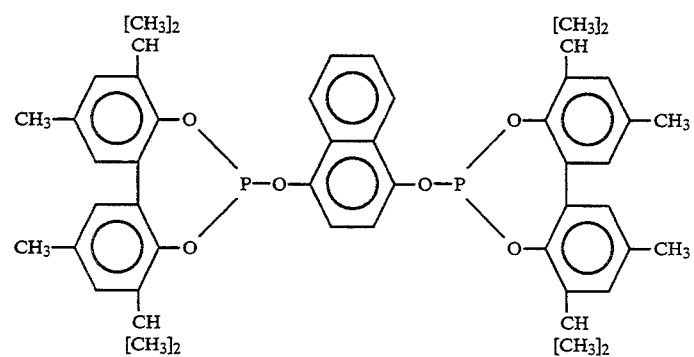

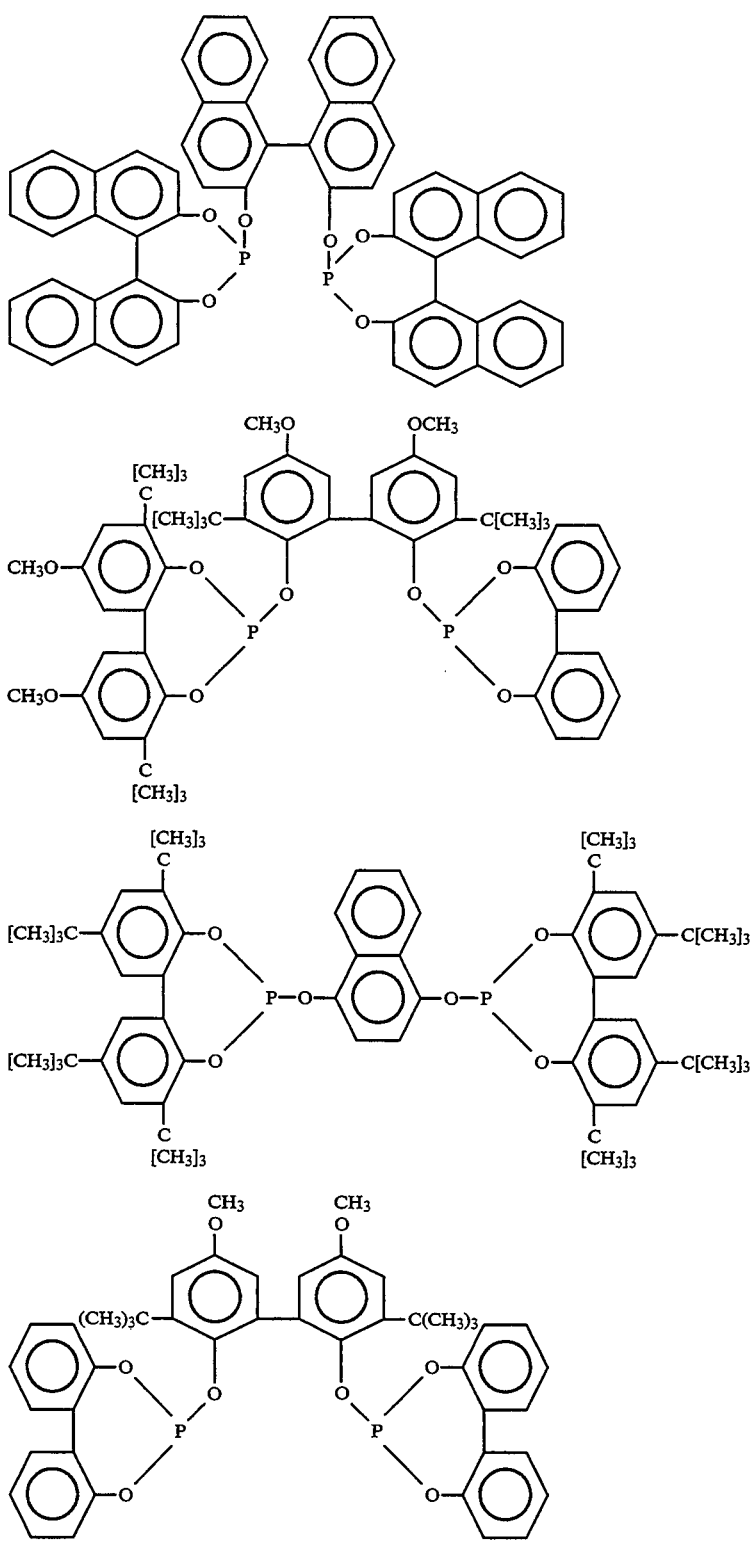

and the like.

Such types of phosphite ligands of the generic class employable in this invention and/or methods for their preparation are known. For instance, the phosphite ligands employable in this invention can be readily and easily prepared via a series of conventional phosphorus halide-alcohol condensation reactions. Such types of condensation reactions and the manner in which they may be conducted are well known in the art. Certain of such preparation methods are set forth in Billig et al U.S. Pat. Nos. 4,668,651; 4,717,775; 4,599,207; and 4,769,498; and 4,885,401; and in Maher et al U.S. Pat. No. 4,774,361.

The amount of ligand employed preferably is sufficient to provide the desired anionic rhodium-containing complex. In producing or preparing the desired complex, an excess of the ligand source may be employed, e.g., to increase the rate of complex formation. In addition, free or uncomplexed ligand, e.g., other than carbon monoxide, may be present during the hydroformylation step. The presence of such free ligand may act to assist in maintaining the active anionic rhodium-containing complex. The molar ratio of such ligand (or ligand source) to rhodium (or rhodium source) is preferably in the range of about 0.1 to about 100, more preferably about 0.5 to about 50, and still more preferably about 0.9 to about 20. very large excesses of ligand source and free ligand are to be avoided as being wasteful. Also, such very large excesses may detrimentally affect the anionic rhodium-containing complex and/or the hydroformylation step.

The present anionic rhodium-containing complex is associated with a cation other than $H^+$ and preferably other than an alkali metal-containing cation, more preferably an organo-containing cation, as described herein.

In one embodiment, the rhodium-containing catalyst is derived from an ionic component which includes one or more of such cations, preferably organo-containing cations. Such ionic components preferably have sufficient basicity, e.g., includes an anion having sufficient basicity, to facilitate formation of the anionic rhodium-containing complex. For example, such anion may have sufficient basicity to deprotonate the hydride rhodium entity which may be provided or produced, e.g., as a precursor of the anionic rhodium-containing complex described herein. The specific anion selected depends, for example, on the specific rhodium source, ligand source, acid, if any, and liquid medium being employed. Preferably, the ionic component is soluble in the liquid medium. Anions associated with medium and strong acids are one class of anions useful in the present ionic components. Specific examples include halides, sulfates, phosphates, carboxylates, in particular low molecular weight carboxylates such as formates, acetates, and the like.

The preferred organo-containing cation can include an element from group Va or group VIa of the periodic chart. One particularly useful group of organo-containing cations are those which have a formula selected from

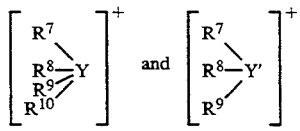

wherein Y is a polyvalent element of group Va of the periodic chart, in particular selected from nitrogen, phosphorus and arsenic, Y' is an element of group VIa of the periodic chart, each of $R^7$, $R^8$, $R^9$ and $R^{10}$ may be the same or different and may combine to form cyclic structures. For example each of $R^7$, $R^8$, $R^9$ and $R^{10}$ may be selected from hydrogen and hydrocarbon or hydrocarbyl radicals which may be substituted or unsubstituted and contain at least 1 carbon atom and, preferably, at least one, and most preferably all, of the hydrocarbon radicals $R^7$, $R^8$, $R^9$ and $R^{10}$ contains at least about 4 carbon atoms, e.g., about 4 to 70 carbon atoms, and sometimes about 4 to 20 carbon, atoms. However, at least one of the $R^7$, $R^8$, $R^9$ and $R^{10}$ substituents must be hydrocarbon-containing.

The hydrocarbon substituents may be aliphatic or aromatic and include, for example, n-hexyl, cyclohexyl, phenyl, benzyl, naphthyl, and the like. Illustrative of the quaternary ammonium and quaternary phosphonium moieties are tetrahydrocarbyl ammoniums, e.g., tetramethyl ammonium, tetraethyl ammonium, tetra-n-propyl ammonium, tetra-n-butyl ammonium, tetra-isobutyl ammonium, trimethyl butyl ammonium, tetraheptyl ammonium, cetyltrimethyl ammonium, tetraphenyl ammonium, trimethylbenzyl ammonium, tetrabenzyl ammonium, tetradodecyl ammonium, tetraoctadecyl ammonium, and the like; trihydrocarbyl ammoniums, e.g., trimethyl ammonium, triethyl ammonium, triphenyl ammonium, tridodecyl ammonium, trioctadecyl ammonium, and the like; dihydrocarbyl ammoniums, e.g., dimethyl ammonium, diethyl ammonium, di-n-butyl ammonium, di-n-heptyl ammonium, diphenyl ammonium, dibenzyl ammonium, didodecyl ammonium, dioctadecyl ammonium, and the like; hydrocarbyl ammoniums, e.g., methyl ammonium, n-butyl ammonium, dodecyl ammonium, octadecyl ammonium, phenyl ammonium, benzyl ammonium, and the like; tetrahydrocarbyl phosphoniums, e.g., tetramethyl phosphonium, tetraethyl phosphonium, tetra-n-propyl phosphonium, tetra-n-butyl phosphonium, tetra-isobutyl phosphonium, trimethyl butyl phosphonium, tetraheptyl phosphonium, tetraphenyl phosphonium, tetrabenzyl phosphonium, tetradodecyl phosphonium, tetraoctadecyl phosphonium, and the like; trihydrocarbyl phosphoniums, e.g., trimethyl phosphonium, triethyl phosphonium, triphenyl phosphonium, tridodecyl phosphonium, trioctadecyl phosphonium, and the like; dihydrocarbyl phosphoniums, e.g., dimethyl phosphonium, diethyl phosphonium, di-n-butyl phosphonium, di-n-heptyl phosphonium, diphenyl phosphonium, dibenzyl phosphonium, didodecyl phosphonium, dioctadecyl phosphonium, and the like; hydrocarbyl phosphoniums, e.g., methyl phosphonium, n-butyl phosphonium, dodecyl phosphonium, octadecyl phosphonium; phenyl phosphonium, benzyl phosphonium, and the like.

Another group of organo-containing cations includes the bis(hydrocarbyl-phosphine)iminiums represented by the formula:

wherein each R11 may be the same or different and may be the same as set for $R^7$ to $R^{10}$. Illustrative of bis(hydrocarbylphosphine)iminiums are bis(triphenylphosphine)iminium, bis(tribenzylphosphine)iminium, bis(trimethylphosphine)iminium, bis(tridodecylphosphine)iminium, and the like and mixtures thereof.

A further group of organo-containing cations have the formula

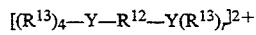

wherein $R^{12}$ is alkylene of 1 to about 6 carbon atoms, each $R^{13}$ is independently selected from hydrogen and hydrocarbyl which may be substituted or unsubstituted, and r is 3. Illustrative examples of this group include the quaternized diamines, the quaterized diphosphines, etc. Specific members of this group include N,N'-bis(trimethyl)propylene diammonium, N,N'-bis(triphenyl)propylene diammonium, N,N'-bis(trioctadecyl)propylene diammonium, P,P'-bis(trimethyl)propylene diphosphonium, and the like and mixtures thereof.

The amount of ionic component, e.g., organo-containing cations, used in producing the present catalyst compositions may vary depending, for example, on the specific ionic component being employed and on the rhodium-containing catalyst desired. The molar ratio of ionic component to rhodium used in producing the present catalyst compositions may vary widely, e.g., in the range of about 0.1 to about 100. The amount of cations present is preferably at least sufficient to combine or couple with the rhodium-containing entity, e.g., the rhodium-containing anion, present to provide the desired catalyst. Excesses of cations, e.g., on the order of at least about 50% or at least about 100% or more, may be utilized.

In one embodiment, the present epoxide hydroformylation contacting occurs in the presence of an electrophile, e.g., $H^+$ ions, protonic acids, Lewis acids and the like and mixtures thereof, in particular, $H^+$ ions in an amount effective to further promote the hydroformylation of the epoxide. Some $H^+$ ions may be present as a result of the deprotonatl0n of the hydride rhodium entity described herein. In certain instances such amounts of $H^+$ ions may be sufficient to provide the desired further epoxide hydroformylation promotion. In a particularly useful embodiment, the epoxide hydroformylation takes place in the presence of an acid, preferably a protonic acid, which can be included in the catalyst composition or catalyst precursor composition.

Medium or strong acids are preferable for use in the present invention. Suitable acids for the process of this invention include such strong acids as sulfuric acid, phosphoric acid, hydroiodic acid, hydrochloric acid, hydrobromic acid, trifluoroacetic acid, p-toluene sulfonic acid, and the like and mixtures thereof. Medium acids suitable for the process include carboxylic acids such as benzoic acid, acetic acid, propionic acid, acidic salts, such as sodium dihydrogen phosphate, and the like and mixtures thereof. Phosphoric acid is a specific example of a useful acid. The amount of acid employed is sufficient to further promote or facilitate epoxide hydroformylation. Such amount may vary depending, for example, on the specific acid and anionic rhodium-containing complex being employed. The molar ratio of acid to rhodium may be in the range of about 0.1 to about 10, preferably about 0.2 to about 3.

The present rhodium-containing catalysts are preferably substantially alkali metal ion-free. In fact, the present 1,3-diol/aldehyde production process, in particular, the hydroformylation step itself, is preferably conducted in the substantial absence of alkali metal ion.

The conditions at which the catalyst composition is produced are such that the desired rhodium-containing catalyst is formed. This preferably takes place in a liquid medium, which preferably acts as a solvent for the rhodium-containing catalyst, and which more preferably acts as a solvent for the rhodium source, the ligand source, the ionic component and the acid, if any, and other components, if any, in the precursor composition used to produce the rhodium-containing catalyst. In one particularly useful embodiment, the liquid medium used in the catalyst precursor composition has substantially the same chemical composition as the liquid medium used in the epoxide hydroformylation contacting step.

The conditions at which the catalyst composition is produced may be similar to those used in the hydroformylation step. The catalyst composition may be prepared separate and apart from the epoxide hydroformylation step and then included in this step to provide the desired catalytic hydroformylation promotion. In one embodiment, a catalyst precursor composition is formed, and this catalyst precursor composition is included in the epoxide hydroformylation step. The hydroformylation conditions are effective to form the catalyst composition from this precursor.

The molar ratio of carbon monoxide to hydrogen employed in the epoxide hydroformylation step may vary widely and may be in the range of about 0.1 to about 10.

In one embodiment, the present process for producing a 1,3-diol and/or a 3-hydroxyaldehyde comprises contacting a combination of an epoxide, carbon monoxide and hydrogen in the presence of a catalyst composition effective to promote the hydroformylation of the epoxide and a promoter component at conditions effective to form at least one of a 1,3-diol and a 3-hydroxyaldehyde. The catalyst composition comprises a ligand-containing anlonlc rhodium-containing complex and an electrophile. The promoter component may be chosen from compounds, complexes, polymeric materials, mixtures thereof and the like. Such promoter component is present in an amount effective to enhance the rate of hydroformylation of the epoxide and/or to enhance the selectivity to the formation of 1,3-diol and/or 3-hydroxyaldehyde. Such enhancement or enhancements are relative to a substantially identical epoxide hydroformylation process performed without, or in the substantial absence of, the presently useful promoter component or components.

Any suitable promoter component or components may be used in the present invention, provided that such component or components are used in concentrations which provide one or more of the enhancements noted elsewhere herein, which concentrations preferably meet the equivalent pH criterion set forth herein. The promoter component is preferably present in the material used in the present contacting step, for example, the reaction mixture, in a molar concentration, for example, moles per liter of liquid, such that the theoretical or equivalent pH of liquid water at 22° C. containing only such molar concentration of such promoter component is in the range of about 1 to about 12, more preferably about 1.6 to about 10.7. Promoter components present in concentrations which provide the above,noted theoretical or equivalent pH values have been found to enhance at least one of the rate of epoxide hydroformylation and the selectivity to 1,3-diol and 3-hydroxyaldehyde. Without wishing to limit the invention to any particular theory of operation, it is believed that such promoter components may act to facilitate the formation and/or maintenance of an effective concentration of the ligand-containing anionic rhodium-containing complex of the catalyst composition at contacting conditions. Conversely, components or concentrations of components which yield either too high or too low a theoretical or equivalent pH, as defined herein, may not effectively facilitate, and may. actually inhibit, the formation and/or maintenance of an effective concentration of the anionic rhodium-containing complex. In any event, promoter components present in amounts to provide the above-noted theoretical or equivalent pH values have been found to be beneficial in the present hydroformylation contacting step.

Although water meets the equivalent pH criterion, and may be employed as a promoter component, the presence of water may irreversibly decompose or alter one or more components of the present catalyst composition at epoxide hydroformylation conditions and/or otherwise detrimentally affect the present process and composition, e.g., detrimentally affect the activity and/or stability of the catalyst composition. The present promoter components are preferably selected so as to have no undue detrimental effect on the present process and composition, in particular so as not to irreversibly decompose or alter one or more components of the present catalyst composition at epoxide hydroformylation conditions. Thus, the promoter component is preferably other than water.

In one embodiment, the promoter component is chosen from those components which alone, or in combination with $H^+$, hydrogen bond with one or more ligands present during the epoxide hydroformylation contacting.

As used herein, the term "promoter component" refers not only to components which are effective to enhance the rate of epoxide hydroformylation and/or the selectivity of the epoxide hydroformylation to 1,3-diol and/or 3-hydroxyaldehyde, but also to one or more materials capable of forming one or more of such components at epoxide hydroformylation conditions.

Particularly useful promoter components are components selected from (a) nitrogen-containing compounds, (b) compounds containing hydroxyl groups, (c) compounds containing carboxyl groups, (d) protonic acids and mixtures thereof. The promoter component or components may include at least one component which is at least two of (a), (b), (c) or (d). Especially useful results are obtained when the promoter component includes at least one hydroxyl group and/or at least one carboxyl group.

Among the useful nitrogen-containing compounds are amines amides, imides, imidazoles, and the like and mixtures thereof. Polymeric nitrogen-containing compounds and mixtures thereof, in particular those polymeric nitrogen-containing compounds which are substantially soluble in the liquid medium present during the epoxide hydroformylation contacting, may also be employed as promoter components. The nitrogen atom or atoms of the nitrogen-containing compounds may be part of a heterocyclic or substituted heterocyclic ring, e.g., containing 4, 5 or 6 or more carbon atoms; and/or may have one or more of such rings and/or one or more saturated, unsaturated or aromatic hydrocarbyl or substituted hydrocarbyl groups bonded, e.g., covalently bonded, thereto. The nitrogen-containing compound may contain one or more than one nitrogen atom. In useful monomeric nitrogen-containing compounds, the number of nitrogen atoms is preferably in the range of 1 to about 5, more preferably 1 to about 3. Compounds with a single nitrogen atom provide useful results. Preferably at least two, and more preferably all three, bonds of at least one of the nitrogen atoms are bonded to hydrocarbyl or substituted hydrocarbyl groups.

Such hydrocarbyl groups and substituted hydrocarbyl groups may contain any number of carbon atoms provided that the promoter Component functions as described herein.in the present invention. In one embodiment, such hydrocarbyl and substituted hydrocarbyl groups contain 1 to about 20, preferably 1 to about 12 carbon atoms. Examples of useful hydrocarbyl groups include alkyl such as methyl, ethyl, propyl, butyl, octyl, decyl and the like; aralkyl, such as phenyl methyl, phenyl ethyl, phenyl butyl, phenyl octyl and the like; aralkenyl such as phenyl ethenyl, phenyl butenyl, phenyl octenyl and the like; alkenyl such as ethenyl, propenyl, butenyl, octenyl, decenyl and the like; alkylene, such as methylene, ethylene, butylene, pentylene, hexylene and the like; other divalent hydrocarbyl groups; aryl, such as phenyl, naphthyl and the like; alkaryl, such as methyl phenyl, ethyl phenyl, butyl phenyl, octyl phenyl and the like; alkenaryl such as ethenyl phenyl, butenyl phenyl, octenyl phenyl and the like; and the like groups. Substituted counterparts of such hydrocarbyl groups may be employed. Such substituents may include, for example, carbon, hydrogen, oxygen, nitrogen, sulfur, halogen, phosphorus, and the like and mixtures thereof.

Specific examples of useful nitrogen-containing promoter components, particularly to enhance the rate of ethylene oxide hydroformylation, include: tris (4-bromophenyl) amine; triphenylamine; benzimidazole; 2,6-lutidine; 2-methylimidazole; 1-methylimidazole; 1,8-his(dimethylamino) naphthalene; triethanolamine; N-methylpyrollidone; dimethylformamide; and the like and mixtures thereof.

Among the useful promoter components which contain hydroxyl groups are those compounds which the hydroxyl group or groups are bonded to a saturated, unsaturated or aromatic hydrocarbyl or substituted hydrocarbyl group. Such hydrocarbyl groups and substituted hydrocarbyl groups may contain any number of carbon atoms provided that the promoter component functions as described herein in the present invention. In one embodiment, such hydrocarbyl and substituted hydrocarbyl groups contain 1 to about 20, preferably 1 to about 12 carbon atoms. Examples of useful hydrocarbyl groups include such groups as are exemplified herein with respect to the nitrogen-containing compounds useful as promoter components. Substituted counterparts of such hydrocarbyl groups may be employed. Such substituents may include, for example, carbon, hydrogen, oxygen, nitrogen, sulfur, halogen, phosphorus, and the like and mixtures thereof.

Enolizable dicarbonyl compounds, such as 2,4-pentanedione and ethyl acetoacetate which exist as two equilibrating tautomers (one of which includes a hydroxyl group) may also be useful as promoter components.

Particularly useful hydroxyl group-containing compounds are chosen from such compounds having at least one aromatic hydrocarbon group. Polymeric compounds and mixtures thereof which include one or more hydroxyl groups, particularly those polymers which are substantially soluble in the liquid medium present during the epoxide hydroformylation contacting, may also be employed as promoter components. The hydroxyl group-containing compound may contain one or more than one hydroxyl group. In monomeric hydroxyl group-containing compounds, the number of hydroxyl groups is preferably in the range of 1 to about 6, more preferably 1 to about 4.

Specific examples of hydroxyl group-containing compounds useful as promoter components include phenol and derivatives of phenol, such as alkyl-, aryl-, and aralkyl-substituted derivatives, for example, o-, m-, and p-cresols, dimethylphenols, ethylphenols, butylated hydroxytoluene and the like; biphenol and derivatives of biphenol, such as alkyland aryl substituted derivatives; substituted biphenols; catechol and derivatives of catechol; resorcinol and derivatives of catechol; resorcinol and derivatives of resorcinol, benzenetriols and derivatives of benzenetriols, such as 1,2,4-benzenetriol; hydroxynaphthalenes, such as 2-naphthol; dihydroxynaphthalenes, such as 1,3-dihydroxynaphthalene; and the like and mixtures thereof.

Among the useful promoter components which contain carboxyl groups are those compounds in which the carboxyl group or groups are bonded to a saturated, unsaturated or aromatic hydrocarbyl of substituted hydrocarbyl group. Such hydrocarbyl groups and substituted hydrocarbyl groups may contain any number of carbon atoms provided that the promoter component functions as described herein in the present invention. In one embodiment, such hydrocarbyl and substituted hydrocarbyl groups contain 1 to about 20, preferably 1 to about 12 carbon atoms. Examples of useful hydrocarbyl groups include such groups as are exemplified herein with respect to the nitrogen-containing compounds useful as promoter components. Substituted counterparts of such hydrocarbyl groups. may be employed. Such substituents may include, for example, carbon, hydrogen, oxygen, nitrogen, sulfur, halogen, phosphorus, and the like and mixtures thereof.

Particularly useful carboxyl groups-containing compounds are chosen from such compounds having at least one aromatic hydrocarbon group, e.g., as described herein. Polymeric compounds and mixtures thereof which include one or more Carboxyl groups, particularly those polymers which are substantially soluble in the liquid .medium present during the epoxide hydroformylation contacting, may also be employed as promoter components. The carboxyl group-containing compounds may contain one or more than one carboxyl group. In monomeric carboxyl group-containing compounds, the number of carboxyl groups is preferably in the range of 1 to about 6, more preferably 1 to about 4.

Specific examples of carboxyl group-containing compounds useful as promoter components include monocarboxylic acids such as acetic acid, propionic acid, butyric acid, isobutyric acid, valeric acid, isovaleric acid, hexanoic acid, decanoic acid, lauric acid, stearic acid, acrylic acid, lactic acid, benzoic acid, p-ethoxybenzoic acid, 3,5-dimethoxybenzoic acid, picolinic acid, pipercolonic acid, cinnamic acid; dicarboxylic acids, such as adipic acid, 1,2-cyclohexane dicarboxylic acid, malonic acid, succinic acid, fumaric acid, glutaric acid, tartaric acid, malic acid, maleic acid, phthalic acid, isophthalic acid, terephthalic acid, and 1,8-naphthalene dicarboxylic acid; polycarboxylic acids, such as polyacrylic acid and 1,3,5-benzene tricarboxylic acid; and the like and mixtures thereof.

Protonic acids, preferably used in concentrations to satisfy the equivalent pH criterion set forth herein, are effective as promoter components. Strong acids, medium strength acids and weak acids all may be employed. Acid salts and other compounds which form protonic acids, e.g., at the contacting conditions, may also be used. Strong protonic acids, in particular acids which are as strong or stronger than phosphoric acid, may be of use in the present invention. Suitable strong acids include sulfuric acid, phosphoric acid, hydroiodic acid, hydrochloric acid, hydrobromic acid, trifluoroacetic acid, p-toluene sulfonic acid, and the like and mixtures thereof. Phosphoric acid is a specific example of a useful acid.

Useful medium strength protonic acids include the carboxylic acids noted previously, as well as phosphorous acid, sulfurous acid, phosphinic acid, phosphonic acids, nitrous acid and the like. Relatively larger concentrations of the medium strength and weak protonic acids are advantageous as compared to the concentrations of the strong acids employed. Examples of weak protonic acids which may be used include biphenol, phenol, butylated hydroxytoluene, succlnimide, carbonic acid, ammonium salts and the like.

The promoter component may include one or more than one other electron withdrawing groups. Examples of electron withdrawing groups useful in the present invention include aromatic hydrocarbon groups, meaning to include therein both substituted and unsubstituted aromatic hydrocarbon groups; fluoroalkyl such as trifluoromethyl and difluoroethyl; fluoroaryl such as fluorophenyl; nitro; chloro; bromo; iodo; carbonyl groups; ester groups; amide groups; carboxylic acid groups; cyano; ammonium (including hydrocarbyl and substituted hydrocarbyl ammonium) groups; phosphonium (including hydrocarbyl and substituted hydrocarbyl phosphonium) groups; sulphonium (including hydrocarbyl and substituted hydrocarbyl sulfonium) groups; and the like and mixtures thereof.

The useful aromatic hydrocarbon group or groups include at least one aromatic hydrocarbyl ring, for example, groups such as aryl groups, alkaryl groups, alkenylaryl groups, aralkyl groups, aralkenyl groups, their substituted counterpart groups, mixtures thereof and the like groups noted elsewhere herein. Groups which include one or more condensed aromatic ring structures are also within the present scope.

The promoter component may include one or more electron donating groups. Examples of electron donating groups useful in the present invention include aikyl groups, such as methyl, ethyl, propyl and butyl; phenyl groups; alkylphenyl groups such as methylphenyl, ethylphenyl, propylphenyl and butylphenyl; alkoxy phenyl groups, such as methoxy phenyl, ethoxy phenyl and propoxy phenyl; aminophenyl groups, such as aminophenyl, methylaminophenyl, dimethylaminophenyl and methyl, ethylamino-phenyl; hydroxyphenyl groups such as hydroxyphenyl and dihydroxyphenyl; amidophenyl; and the like and mixtures thereof.

As used herein the electron withdrawing ability or electron donating ability of any given group or substituent is as compared to a hydrogen atom substituent at epoxide hydroformylation conditions. That is, an electron withdrawing group is defined as being able to more strongly withdraw electrons relative to a hydrogen atom substituent. Similarly, an electron donating group is defined as being able to more easily give up one or more electrons relative to a hydrogen atom substituent and the like.

The inclusion of one or more electron withdrawing groups, and/or electron donating groups may act to control the acidity/basicity of a particular component so as to enable compliance with the acidity/basicity constraints of the present promoter components.

Particularly useful promoter components are selected from triethanolamine, 2,6-lutidine, benzimidazole, 2-methylimidazole, biphenol, catechol isophthalic acid, picolinic acid, acetic acid, p-ethoxybenzoic acid, dimethylformamide, N-methylpyrolidone and mixtures thereof.

The amount of promoter component used should be sufficient to provide the desired results and preferably to satisfy the equivalent pH criterion set forth herein. Care should be exercised to avoid excessive amounts of promoter component. Such excessive amounts of promoter component may provide little or no additional benefit and/or may have an overall detrimental effect on the present system. Also, the cost of the promoter component may mitigate against its use in large amounts. In one useful embodiment, the promoter component is present in an amount so that the molar ratio of promoter component to rhodium is in the range of about 0.1 to about 10. In particular, the molar ratio of nitrogen atoms, hydroxyl groups, carboxyl groups and/or $H^+$ present in the promoter component to rhodium is in the range of about 0.1 to about 10.

The 3-hydroxyaldehyde produced in the epoxide hydroformylation may be recovered, e.g., using one or more conventional recovery techniques, from the liquid medium and other components which are present during or after the hydroformylation contacting. Further, the 3-hydroxyaldehyde can be hydrogenated, e.g., using conventional hydrogenation processing, to yield the desired 1,3-diol.

The hydrogenation step of the present invention is usually conducted under specified conditions of time and temperature. Preferably, hydrogenation temperature is in the range of about 90° to about 170° C., preferably for a period of time in the range of about 0.5 to about 4 hours. The hydrogenation reaction can be carried out with or without a hydrogenation liquid medium. The hydrogenation liquid medium preferably is water, although nonreactive polar organic solvents, such as dimethoxyethane and the like, can be used. The pressure employed during hydrogenation is preferably in the range of about 500 to about 2,000 psig. The catalyst used in the hydrogenation step can be any of the well known hydrogenation catalysts used in the art, such as Raney nickel, palladium, platinum, ruthenium, rhodium, cobalt and the like. It is desirable to employ as the hydrogenation catalyst a metal or a compound of a metal which may be easily and economically prepared, which has a high degree of activity, and which retains this activity for extended periods of time. The hydrogenation catalyst may be employed in a finely divided form and dispersed throughout the reaction mixture, or it may be employed on a support or carrier material such as diatomaceous earth, clay, alumina, carbon or the like.. The amount of hydrogenation catalyst used is preferably in the range of about 0.1% to about 10% more preferably about 1% to about 8%, by weight of the 3-hydroxyaldehyde to be hydrogenated.

The present invention is further illustrated by the following non-limiting examples.

In the examples the indicated names are used to refer to the following ligands

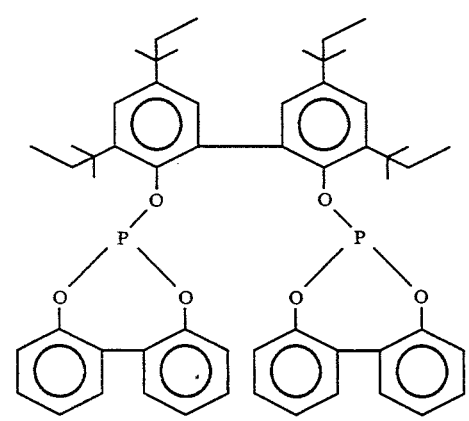

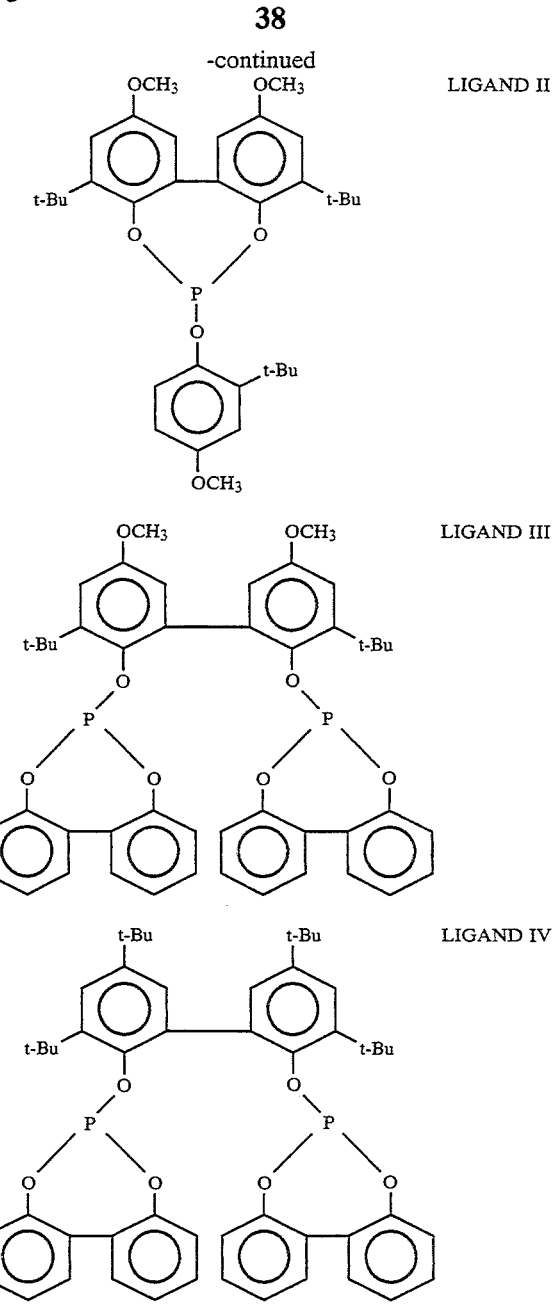

EXAMPLE 1

A hydroformylation catalyst precursor was synthesized by combining 0.52 g of rhodium dicarbonyl acetylacetonate [Rh(CO)$_2$ (acac)], 0.643 g of tetrabutylphosphonium acetate [Bu$_4$P][OAc], 1.693 g of Ligand IV and 5 cc of water in 80 cc of dimethoxyethane. This catalyst precursor was tested as follows.

A stirred 300 cc autoclave, made of a suitably resistant metallic alloy such as stainless steel or Hastelloy-C TM, and equipped with internal cooling coils, a thermocouple and a pressure measuring device was used for the treating. The catalyst precursor and ethylene oxide were mixed in a Schlenk flask, and then pressurized into the autoclave through a valve in the head of the autoclave. The autoclave was then mounted in position and the appropriate amount of a mixture of carbon monoxide and hydrogen was introduced. The autoclave was heated to the desired temperature, and the pressure was adjusted, as necessary to maintain the desired pressure, by further additions of the $CO/H_2$ mixture or by venting. As the hydroformylation reaction progressed, additional amounts of the $CO/H_2$ mixture were added until the desired gas consumption or reaction time was achieved. After the reaction, the autoclave was cooled, e.g., to about $-40°$ C., and excess gas pressure was vented. After warming to about $0°$ C., the autoclave was opened and the contents analyzed using conventional techniques.

Using the catalyst precursor described above, 10 g of ethylene oxide was contacted in the autoclave at $110°$ C. and 1000 psig pressure of a synthesis gas, $CO/H_2$, mixture having a mole ratio of 1 CO to 2 $H_2$. Gas uptake began substantially immediately and no induction period was apparent.

This reaction resulted in a selectivity of ethylene oxide to 3-hydroxypropionaldehyde and 1,3-propanediol of 44 mole %. Rate of formation of 3-hydroxypropionaldehyde and 1,3-propanediol was equal to 0.33 moles/liter/hour.

EXAMPLE 2

Example 1 was repeated except that the catalyst precursor was synthesized without water and tetraglyme replaced the dimethoxyethane. This reaction resulted in a selectivity of ethylene oxide to 3-hydroxypropionaldehyde and 1,3-propanediol of 38 mole % and a rate of formation of 3-hydroxypropionaldehyde and 1,3-propanediol of 0.19 moles/liter/hour. These results indicate that water can have an enhancing effect on the activity and selectivity of the catalyst composition or system.

EXAMPLE 3

Example 1 was repeated except that no tetrabutylphosphonium acetate, [Bu$_4$P][OAc], was used. Substantially no ethylene oxide hydroformylation was observed. These results indicate that an ionic component is important in an effective epoxide hydroformylation catalyst system.

EXAMPLES 4 AND 5

Example 2 was repeated twice except that Ligand III (Example 4) and Llgand I (Example 5) were used in place of Ligand IV, and the hydroformylation reaction was conducted at one-half catalyst precursor concentration relative to that in Example 2.

Results of these tests were as follows

| Example | Selectivity to 3-Hydroxypropionaldehyde, and 1,3-Propanediol mole % | Rate of Formation of 3-Hydroxypropionaldehyde, and 1,3-Propanediol moles/liter/hour |
| --- | --- | --- |
| 4 | 40 | 0.14 |
| 5 | 50 | 0.10 |

These results indicate that various bis-phosphite ligands are useful in producing epoxide hydroformylation catalyst systems.

EXAMPLE 6

Example 2 was repeated except that the hydroformylation reaction was terminated when only 25% of the ethylene oxide was converted. In Example 2 substantially all of the ethylene oxide had been converted. Results of Example 6 were a selectivity of ethylene oxide to 3-hydroxypropionaldehyde and 1,3-propanediol of 75 mole % and a rate of formation of 3-hydroxypropionaldehyde and 1,3-propanediol of 0.8 moles/liter/hour. These results demonstrate that reduced epoxide conversions provide increased rates of product formation and increased selectivity to the desired product or products.

EXAMPLE 7

Example 2 was repeated except that toluene was used instead of tetraglyme, the reaction temperature was $115°$ C., and 2 mmols of 2,6-lutidine was included in the reaction mixture. The molar concentration of 2,6-lutidine was such that the equivalent pH of a 2,6-lutidine/water solution would be about 9.5. Substantial ethylene oxide hydroformylation occurred, yielding substantial amounts of 3-hydroxypropionaldehyde. Upon opening the autoclave, it was determined that the product 3-hydroxypropionaldehyde had formed a separate phase from the toluene solvent.

The product 3-hydroxypropionaldehyde (19.5 mmols) was separated from the toluene solvent. This separated 3-hydroxypropionaldehyde was added to 10 ml of water and transferred to a glass lined 300 ml autoclave. To this autoclave was added 0.27 g of Raney 3100 molybdenum promoted nickel catalyst in 30 ml of water. The pH was adjusted to 7 by the addition of 3 normal sulfuric acid. The autoclave reactor was sealed and pressurized to 1000 psi hydrogen at $20°$ C. The contents were heated to $105°$ C. and maintained at this temperature for 3 hours. The reaction was then cooled to $20°$ C. and the contents were analyzed. It was found that 1,3-propanediol had formed at a yield of 96%.

The substantial activity of the present catalyst composition for promoting the hydroformylation of ethylene oxide in toluene is surprising since other work, i.e., Murphy, et al U.S. Pat. Nos. 4,873,378 and 4,873,379, indicate that solvents such as toluene are less suited to hydroformylation of low molecular weight epoxides. The present system, in particular the present catalyst system, is substantially different from, and provides unexpected advantages relative to, this other work.

EXAMPLE 8

1.0 g of $Rh_4(CO)_{12}$ and 4.44 g of Ligand IV were charged to a 300 cc Parr autoclave. The autoclave was sealed, and then purged with nitrogen. 40 cc of heptane was pressurized into the autoclave through a suitable valve, and the autoclave was flushed with 1:1 $CO/H_2$ gas mixture before being pressurized to 60 psig with this gas mixture. The autoclave was stirred overnight at ambient temperature. The autoclave was then opened, the off-white precipitate was collected and washed with hexane solvent and dried under vacuum. The product was determined to be $HRh(CO)_2$(Ligand IV).

To a stirred mixture of 0.3 g of potassium hydroxide in 30 cc of methanol under nitrogen was added 1.0 g of $HRh(CO)_2$ (Ligand Iv) followed by 23 g of bis(triphenylphosphine)iminium chloride, [PPN][Cl]. The mixture was stirred at ambient temperature for 5 hours, after which time the insoluble product was isolated by filtration. It was washed with methanol, diethyl ether and then dried under vacuum. This product was determined to be [PPN][Rh(CO)$_2$(Ligand IV)].

Example 2 was repeated except that 1 mmol of [PPN][Rh(CO) (Ligand IV)] was used as the catalyst precursor. Substantially no gas uptake was observed after 50 minutes. Substantially no H+ions were present during the hydroformylation reaction.

EXAMPLE 9

Example 8 was repeated except that 0.06 g of acetic acid was included in the 300 cc autoclave. The molar concentration of acetic acid was such that the equivalent pH of an acetic acid/water solution would be about 3.4. Results of this test were a selectivity of ethylene oxide to 3-hydroxyproplonaldehyde and 1,3-propanediol of 26 mole % and a rate of formation of 3-hydroxyproplonaldehyde and 1,3-propanediol of 0.05 moles/liter/hour. These results indicate that the presence of acetic acid in the above-noted concentration can enhance the promotion of epoxide hydroformylation.

EXAMPLE 10

Example 8 was repeated except that equimolar amounts of [PPN][Rh(CO)$_2$(Ligand IV)] and [HRh(CO)$_2$(Ligand IV)] were used instead of only [PPN][Rh(CO)$_2$(Ligand IV)] and the mole ratio of CO to H$_2$ was 0.25. Results of this test were a selectivity of ethylene oxide to 3-hydroxypropionaldehyde and 1,3-propanediol of 37 mole % and a rate of formation of 3-hydroxypropionaldehyde and 1,3-propanediol of 0.055 moles/liter/hour.

EXAMPLE 11 (COMPARATIVE)

A hydroformylation catalyst precursor was synthesized by combining 0.51 g of rhodium dicarbonyl acetylacetonate, Rh(CO)$_2$(acac), 0.53 g of tricyclohexylphosphine, (Cy)$_3$P, 0.13 g of phosphoric acid, H$_3$PO$_4$, 5 cc of water, and 0.1 g of hydroquinone in 80 g of tetraglyme solvent. This formulation was substantially the same as that reported in Example 6 of Murphy et al U.S. Pat. No. 4,873,378.

Example 1 was repeated using the catalyst precursor prepared above instead of the catalyst precursor prepared in Example 1. An induction period of about 30 minutes occurred before gas uptake began. During this induction period, it is believed that the catalyst precursor reacted with ethylene oxide to form an active ethylene oxide hydroformylation catalyst which itself includes ethylene oxide molecules and/or one or more parts thereof. Results of this test were a selectivity to 3-hydroxypropionaldehyde and 1,3-propanediol of 59% and a rate (not including the induction period) of 3-hydroxypropionaldehyde and 1,3-propanediol formation of 0.08 moles/liter/hour. In Example 11, 1,3-propanediol was produced in a greater amount than 3-hydroxyproplonaldehyde, while the reverse was true in Example 1.

EXAMPLES 12 TO 15

A series of rhodium-containing catalyst precursors were prepared. Each of these catalyst precursors was prepared by combining the components noted below in 80 cc of dimethyoxyethane. Each of the catalyst precursors was produced using 2 mmol of rhodium dicarbonyl acetylacetonate, Rh(CO)$_2$(acac)], 2 mmol of tetrabutylphosphonium acetate, Bu$_4$P][OAc], 2 mmol of phosphoric acid, H$_3$PO$_4$, and 5 cc of water. These catalyst precursors included the following ligands

| Example | Ligand | Amount of Ligand |
|---|---|---|
| 12 | Ligand II | 2 mmol |
| 13 | PMe$_3$[1] | 2 mmol |
| 14 | P(OMe)$_3$[2] | 2 mmol |
| 15 | Bu$^t$NC[3] | 2 mmol |

[1] Trimethylphosphine
[2] Trimethylphosphite
[3] Tertiarybutylisonitrile

Each of these catalyst precursors was tested in ethylene oxide hydroformylation service using a procedure generally as described in Example 1. The molar concentration of phosphoric acid was such that the equivalent pH of a phosphoric acid/water solution would be about 1.8. The contacting was conducted at the following conditions:

| | |
|---|---|
| Pressure | 1000 psig |
| Temperature | 110° C. |
| CO/H$_2$(molar) | 1:2 |
| Rhodium concentration | 2000 ppm by weight |

Results of these tests were as follows:

| Example | Ligand | Selectivity to 3-Hydroxypropionaldehyde and 1,3-Propanediol, mole % | Rate of Formation of 3-Hydroxypropionaldehyde and 1,3-Propanediol, moles/liter/hour |
|---|---|---|---|
| 12 | Ligand II | 40 | 0.08 |
| 13 | PMe$_3$ | 35 | 0.18 |
| 14 | P(OMe)$_3$ | 55 | 0.14 |
| 15 | Bu$^t$NC | 10 | 0.02 |

These results indicate that the phosphite ligands (Examples 12 and 14) provide increased product selectivity relative to the non-phosphite ligands (Examples 13 and 15). With reference to Example 1, the bis-phosphites provide highly effective product formation rates and selectivities relative to other phosphite ligands and to the nOn-phosphite ligands.

EXAMPLES 16 TO 31

Another series of rhodium-containing compositions were prepared. Each of these catalyst precursors Was prepared by combining the. components noted below in 80 cc of tetraglyme. Each of the catalyst precursors was produced using 2 mmol of rhodium dicarbonyl acetylacetonate, Rh(CO)$_2$(acac), 2 mmol of tetrabutylphosphonium acetate, [Bu$_4$P][OAc], and 2 mmol of the ligand indicated below.

Each of these catalyst precursors was tested in ethylene oxide hydroformylation service using a procedure generally as described in Example 1. Except as otherwise indicated, the contacting was conducted at the following conditions:

| | |
|---|---|
| Pressure | 1000 psig |
| Temperature | 110° C. |
| CO/H$_2$ (molar) | 1:2 |
| Rhodium concentration | 2000 ppm by weight |

-continued

| Example | Ligand | Rate of Formation of 3-Hydroxypropionaldehyde, and 1,3-propanediol moles/liter/hour | |
|---|---|---|---|
| | Water | 5 cc | |

Results of these tests were as follows:

| Example | Ligand | Rate of Formation of 3-Hydroxypropionaldehyde, and 1,3-propanediol moles/liter/hour | |
|---|---|---|---|
| 16 | Ligand IV | 0.23 | No water |
| 17 | DIPHOS monoxide[1] | 0.08 | Much heavy material produced |
| 18 | Dipyridyl[2] | 0.020 | |
| 19 | OP (cyclohexyl)$_3$ | 0.028 | |
| 20 | DIARS[3] | 0.015 | |
| 21 | Ph$_2$P(O)CH$_2$P(O)Ph$_2$ | 0.026 | |
| 22 | Polyvinylalcohol | 0.023 | |
| 23 | Ph$_2$P(O)CH$_2$CH$_2$P(O)Ph$_2$ | 0.023 | |
| 24 | Ph$_2$P(O)CH$_2$CH$_2$PPh$_2$ | Low | No 3-Hydroxypropionaldehyde or 1,3-Propanediol identifiable |
| 25 | Ph$_2$PH | 0.008 | |
| 26 | CN$^-$ | 0.006 | |
| 27 | PO(octyl)$_3$ | 0.005 | |
| 28 | 2,6-lutidine[4] | 0.003 | |
| 29 | Bu$^t$SH | 0.003 | |
| 30 | P(o-tolyl)$_3$ | 0.002 | |
| 31 | P(o-MeOphenyl)$_3$ | 0.000 | |

[1] Ph$_2$PCH$_2$CH$_2$PPh$_2$ with P=O

[2] 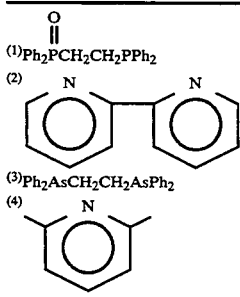

[3] Ph$_2$AsCH$_2$CH$_2$AsPh$_2$

[4] (pyridine structure)

These results indicate that the choice of ligand is important in obtaining an effective epoxide hydroformylation catalyst.

EXAMPLES 32 TO 43

Example 2 was repeated 12 times except that 2 mmols of a different nitrogen-containing compound, as indicated below, was included with the catalyst. Also, these catalyst precursors were tested in ethylene oxide hydroformylation service at 115° C. and 900–1000 psig pressure of a synthesis gas mixture having a mole ratio of 1 CO to 4.3 H$_2$.

Results of these tests were as follows:

| Example | Amine[2] | Selectivity to 3-Hydroxypropionaldehyde and 1,3-Propanediol mole % | Rate of Formation of 3-Hydroxypropionaldehyde and 1,3-Propanediol moles/liter/hour |
|---|---|---|---|
| 32 | Tris(4-bromophenyl)amine (7.0) | 55 | 0.47 |
| 33 | Triphenylamine (7.0) | 48 | 0.50 |
| 34 | Benzimidazole (8.9) | 44 | 0.69 |
| 35 | 2,6-Lutidine (9.5) | 51 | 0.69 |
| 36 | 2-Methylimidazole (6.6) | 33 | 0.70 |
| 37 | 1-Methylimidazole (9.7) | 31 | 0.45 |
| 38 | Dimethylbenzylamine (10.6) | 51 | 0.72 |
| 39 | Tetramethylethylenediamine (10.7) | 21 | 0.24 |
| 40 | Triethylamine (11.0) | 19 | 0.22 |
| 41 | Tetramethylpropylenediamine (11.0) | 17 | 0.25 |
| 42 | DABCO[1] (11.6) | 24 | 0.30 |
| 43 | 1,8-Bis(dimethylamino)naphthalene (12.1) | 42 | 0.42 |
| Control | None | 50 | 0.3 |

(1) 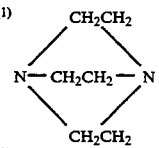

[2] The number in parenthesis after the name of the nitrogen-containing compound is the approximate equivalent pH of a water solution containing the same molar concentration of the amine as is present in the reaction mixture.

The results indicate that certain amounts of certain nitrogen-containing compounds affect the selectivity and/or rate of formation of 3-hydroxypropionaldehyde and 1,3-propanediol in the hydroformylation of ethylene oxide. In particular, the presence of such compounds in amounts such that the equivalent pH would be about 12 or less, preferably about 10.7 or less, provide an enhanced rate of formation of 3-hydroxypropionaldehyde and 1,3-propanediol. The presence of such amounts of certain of these nitrogen-containing compounds also provides enhanced ethylene oxide hydroformylation selectivity to 3-hydroxypropionaldehyde and 1,3-propanediol. With regard to Example 43, it is believed (without wishing to limit the invention to any particular theory of operation) that 1,8-bis(dimethylamino) naphthalene, for example, because of the compound's inherent steric hinderance, acts as a less basic component than would be predicted by the equivalent pH. Consequently, although the equivalent pH is slightly above 12, 1,8-bis (dimethylamino) naphthalene does provide some degree of enhancement in the rate of formation of 3-hydroxypropionaldehyde and 1,3-propanediol.

EXAMPLES 44 TO 49

A series of ethylene oxide hydroformylation experiments were run in accordance with the general procedure outlined in Example 1 with no water present.

The catalyst precursor used was:
2 mmol of rhodium dicarbonyl acetylacetonate
5 mmol of Llgand IV
3 mmol of tetrabutylphosphonium acetate
3 mmol of 2,6-lutidine 100 cc of tetraglyme solvent was employed. The molar concentration of 2,6-lutidine was such that the equivalent pH of a 2,6-lutidine/water solution would be about 9.6. The reaction conditions were as follows:
Pressure: 1000 psig
Temperature: 115° C.
CO/H$_2$ (molar): 1:2
Ethylene oxide: varied as indicated below
Results of these experiments were as follows:

| Example | Ethylene oxide, moles/liter | Selectivity to 3-Hydroxypropionaldehyde and 1,3-Propanediol, mole % | Rate of Formation of 3-Hydroxypropionaldehyde and 1,3 Propanediol, moles/liter/hour |
|---|---|---|---|
| 44 | 1.09 | 66 | 0.43 |
| 45 | 2.06 | 67 | 0.99 |
| 46 | 2.97 | 64 | 1.40 |
| 47 | 3.79 | 64 | 1.70 |
| 48 | 4.55 | 61 | 2.21 |
| 49[1] | 6.14 | 57 | 3.47 |

[1]In Example 49, 73 g of tetraglyme was employed.

These results indicate that the concentration of ethylene oxide does affect the activity and selectivity of the catalyst system.

EXAMPLES 50 AND 51

Two (2) ethylene oxide hydroformylation experiments were run in accordance with the general procedure outlined in Example 1 with no water present.
The catalyst precursor used was:
2 mmol of rhodium dicarbonyl acetylacetonate
2 mmol of Ligand IV
2 mmol oftetrabutylphosphonium acetate
Phosphoric acid-varied as indicated below
100 cc of tetraglyme solvent was employed. The reaction conditions were as follows:
Pressure: 1000 psig
Temperature: 110° C.
CO/H$_2$(molar): 1:2
Ethylene oxide: 10 g
Results of these experiments were as follows:

| Example | H$_3$PO$_4$,[1] mmols | Selectivity to 3-Hydroxypropionaldehyde and 1,3-Propanediol, mole % | Rate of Formation 3-Hydroxypropionaldehyde and 1,3-Propanediol, moles/liter/hour |
|---|---|---|---|
| 50 | 2.0 (1.8) | 67 | 0.12[2] |
| 51 | 5.0 (1.5) | 51 | 0.01[3] |

[1]The number in parenthesis after the number of mmols of phosphoric acid is the approximate pH of a water solution containing the same molar concentration of phosphoric acid as is present in the reaction mixture.
[2]An induction period of 23 minutes occurred before gas uptake began. The rate listed does not include the induction period.
[3]An induction period of 35 minutes occurred before gas uptake began. The rate listed does not include the induction period.

These results indicate that while a limited amount of phosphoric acid, in particular such amount as would provide an equivalent pH of about 1.6 or greater, in the catalyst system provides benefits, e.g., enhanced rates and/or selectivities, an excessive amount of phosphoric acid can be detrimental to the ethylene oxide hydroformylation reaction.

EXAMPLE 52

Example 50 was repeated except that the catalyst precursor included 2 mmols of triethanolamine and no phosphoric acid. The molar concentration of triethanolamine was such that the equivalent pH of a triethanolamine/water solution would be about 10.0. Results of this experiment were as follows

| Selectivity to 3-Hydroxypropionaldehyde and 1,3-Propanediol, mole % | Rate of Formation of 3-Hydroxypropionaldehyde and 1,3-Propanediol, moles/liter/hour |
|---|---|
| 73 (74)[1] | 0.74 (0.76)[1] |

[1]The values in parenthesis are from an exact duplicate experiment.

These results indicate that triethanolamine promotes ethylene oxide hydroformylation, and that the experimental procedure used provides substantially reproducible results. In particular, the presence of triethanolamine in the above-noted concentration provides for an enhanced rate of ethylene oxide hydroformylation and enhanced selectivity to 3-hydroxypropionaldehyde and 1,3-propanediol.

EXAMPLES 53 AND 54

Example 2 was repeated two times except that 2 mmols of biphenol was included with the catalyst. The molar concentration of biphenol was such that the equivalent pH of a biphenol/water solution would be about 5.4. In Example 54 the hydroformylation reaction was conducted at 90° C.
Results of these tests were as follows:

| Example | Selectivity to 3-Hydroxypropionaldehyde and 1,3-Propanediol, mole % | Rate of Formation of 3-Hydroxypropionaldehyde and 1,3-Propanediol, moles/liter/hour |
|---|---|---|
| 53 | 73 | 0.54 |
| 54 | 85 | 0.19 |

These results indicate that certain concentrations of certain other components, in particular biphenol in the abovenoted concentration, affect the selectivity and/or rate of formation of 3-hydroxypropionaldehyde and 1,3-propanediol in the hydroformylation of ethylene oxide.

In addition, lower hydroformylation temperatures may result in increased selectivity.

EXAMPLE 55

The 3-hydroxypropionaldehyde product from Example 47 is recovered, e.g., by distillation, and subjected to further processing as follows. This 3-hydroxypropionaldehyde (10.9 mmols) is added to 9 ml of water and transferred to a glass lined 300 ml autoclave. To this autoclave reactor is added 0.14 g of Raney 3100 molybdenum promoted nickel catalyst in 30 ml of water. The pH was adjusted to 7 by the addition of 3 normal sulfuric acid. The autoclave reactor is sealed and pressurized to 1000 psi at 22° C. The contents are heated to 105° C. and are maintained at this temperature for 2 hours. After this time, the temperature is raised to 160° C. and maintained at this temperature for 1 hour. The reactor is then cooled to 25° C. and the contents are analyzed. It is found that 1,3-propanediol is produced in 95% yield.

EXAMPLES 56 TO 63

Example 50 was repeated a number of times except that the catalyst precursor in each repetition included 2 mmols of a different one of varigds compounds, as indicated below, and no phosphoric acid. Results of these experiments were as follows:

| Example | Added[1] Component | Selectivity to 3-Hydroxypropionaldehyde and 1,3-Propanediol, mole % | Rate of Formation of 3-Hydroxypropionaldehyde and 1-3-Propanediol, moles/liter/hour |
|---|---|---|---|
| 56 | Picolinic Acid (2.6) | 71 | 0.78 |
| 57 | Acetic Acid (3.2) | 72 | 0.88 |
| 58 | Dimethylformamide (7.1)[2] | 73 | 0.80 |
| 59 | N-Methylpyrollidone (7.1)[2] | 72 | 0.81 |
| 60 | Catechol (5.4) | 68 | 0.59 |
| 61 | p-Ethoxybenzoic Acid (3.2) | 65 | 0.70 |
| 62 | 3,5-Dimethoxybenzoic Acid (3.2) | 62 | 0.67 |
| 63 | Isophthalic Acid (2.7) | 61 | 0.69 |

[1]The number in parenthesis after the name of the added component is the approximate equivalent pH of a water solution containing the same molar concentration of such added component as is present in the reaction mixture.
[2]The equivalent pH was experimentally determined.

Each of the compounds tested at the concentrations employed provided an enhanced rate of epoxide hydroformylation. In addition, such concentrations of these compounds provided enhanced selectivities to the desired 3-hydroxypropionaldehyde and 1,3-propanediol products.

While this invention has been described with respect to various specific examples and embodiments, it is to be understood that the invention is not limited thereto and that it can be variously practiced within the scope of the following claims.

What is claimed is:

1. A catalyst composition comprising, in a liquid medium, i) an anionic complex of rhodium and a ligand containing phosphorus and oxygen and ii) an electrophile selected from H+ions, protonic acids, Lewis acids, or mixtures thereof, said catalyst composition having catalytic activity to promote the hydroformylation of an epoxide.

2. The catalyst of claim 1, wherein the ligand is a phosphite ligand.

3. The catalyst of claim 1, wherein the ligand a bisphosphite ligand.

4. The catalyst of claim 1, wherein the electrophile is a protonic acid.

5. The catalyst of claim 4, wherein the protonic acid is acetic acid.

6. The catalyst of claim 4, wherein the protonic acid is phosphoric acid.

7. The catalyst of claim 4, wherein the protonic acid is a mixture of acetic acid and phosphoric acid.

8. The catalyst of claim 1, wherein the electrophile is a Lewis acid.

9. A process for producing a rhodium-containing catalyst composition, comprising contacting in a liquid medium i) a rhodium source, ii ) a source of ligand containing phosphorus and oxygen and iii) an ionic component including an organo-containing cation, at conditions effective to produce an anionic complex of rhodium and a ligand containing phosphorus and oxygen, said anionic complex having catalytic activity to promote the hydroformylation of an epoxide in the presence of an electrophfie.

10. The process of claim 9, wherein said contacting takes place in the presence of a promoter component selected from the group consisting of (a) nitrogen-containing compounds, (b) compounds containing hydroxyl groups, (c) compounds containing carboxyl groups, (d) protonic acids and mixtures thereof.

11. The process of claim 10, wherein the promoter component is selected from the group consisting of triethanolamine, 2,6-lutidine, benzimidazole, 2-methylimidazole, biphenol, catechol, isophthalic acid, picolinic acid, acetic acid, p-ethoxybenzoic acid, dimethylformamide, N-methylpyrollidone and mixtures thereof.

12. The process of claim 9, wherein the contacting occurs in the presence of at least one of carbon monoxide and hydrogen.

13. The process of claim 9, wherein the source of ligand provides a phosphite ligand.

14. The process of claim 9, wherein the organo-containing cation contains an element from group Va or group VIa of the periodic chart.

* * * * *